US012390627B2

(12) United States Patent
Azdoud et al.

(10) Patent No.: US 12,390,627 B2
(45) Date of Patent: Aug. 19, 2025

(54) ROBOTIC TATTOOING MACHINE WITH AN OPTICAL TATTOO ANALYZER TO ANALYZE TATTOOS ASSOCIATED WITH NON-FUNGIBLE TOKENS

(71) Applicant: Blackdot, Inc., Austin, TX (US)

(72) Inventors: Yan Azdoud, Austin, TX (US); Joel Richard Pennington, Austin, TX (US); Deniz Ozturk, Philadelphia, PA (US)

(73) Assignee: Blackdot, Inc., Austin, TX (US)

( * ) Notice: Subject to any disclaimer, the term of this patent is extended or adjusted under 35 U.S.C. 154(b) by 478 days.

(21) Appl. No.: 17/752,701

(22) Filed: May 24, 2022

(65) Prior Publication Data

US 2022/0370778 A1 Nov. 24, 2022

Related U.S. Application Data

(60) Provisional application No. 63/192,534, filed on May 24, 2021.

(51) Int. Cl.
*G06F 21/00* (2013.01)
*A61M 37/00* (2006.01)
(Continued)

(52) U.S. Cl.
CPC ........ *A61M 37/0076* (2013.01); *B25J 9/1697* (2013.01); *G06F 21/10* (2013.01);
(Continued)

(58) Field of Classification Search
CPC ..... G06F 21/335; G06F 21/16; H04L 9/3213; H04L 9/3247; H04L 9/50; A61M 37/0076
(Continued)

(56) References Cited

U.S. PATENT DOCUMENTS

| 2,735,780 A | 2/1956 | Le Compte et al. |
| 3,640,889 A | 2/1972 | Stewart |

(Continued)

FOREIGN PATENT DOCUMENTS

| WO | 2008085758 | 7/2008 |
| WO | 2015193513 | 12/2015 |

(Continued)

OTHER PUBLICATIONS

ISA: United States Patent and Trademark Office, International Search Report and Written Opinion, PCT Application No. PCT/US2020/043588, mailed Oct. 30, 2020, 13 pages.

(Continued)

*Primary Examiner* — Jeffrey C Pwu
*Assistant Examiner* — Samuel Ambaye
(74) *Attorney, Agent, or Firm* — Perkins Coie LLP

(57) ABSTRACT

Art Non-Fungible Tokens (NFTs) are typically associated with the ownership of the digital art. NFTs can be used in the field of tattooing to manage a tattoo client, art generation, art conversion into tattoo instructions, manage payment of stakeholders, allow a client to buy and sell tattoos in a secondary market, book/manage tattoo sessions, or combinations thereof. An NFT structure allows for the certification of ownership. For the context of tattooing, a smart contract may be used to track ownership of the digital design rendition of the tattoo and tattooing information. The NFT smart contract may contain the rights for the execution of the tattoo, which may allow one or many applications of a tattoo rendition of the NFT digital design, such right being consumed in the process of successive executions until the NFT may not contain any rights associated with tattooing.

20 Claims, 10 Drawing Sheets
(1 of 10 Drawing Sheet(s) Filed in Color)

(51) Int. Cl.
  *B25J 9/16* (2006.01)
  *G06F 21/10* (2013.01)
  *G06F 21/16* (2013.01)
  *G06F 21/33* (2013.01)
  *H04L 9/00* (2022.01)
  *H04L 9/32* (2006.01)

(52) U.S. Cl.
  CPC ............ *G06F 21/16* (2013.01); *G06F 21/335* (2013.01); *H04L 9/3213* (2013.01); *H04L 9/3247* (2013.01); *H04L 9/50* (2022.05); *A61M 2205/6063* (2013.01); *H04L 2209/603* (2013.01)

(58) Field of Classification Search
  USPC ........................................................ 713/185
  See application file for complete search history.

(56) References Cited

U.S. PATENT DOCUMENTS

| | | |
|---|---|---|
| 3,873,687 A | 3/1975 | Demko |
| 4,155,886 A | 5/1979 | DeGoler |
| 4,204,438 A | 5/1980 | Binaris et al. |
| 4,610,806 A | 9/1986 | Rosen |
| 4,894,547 A | 1/1990 | Leffell et al. |
| 5,401,242 A | 3/1995 | Yacowitz |
| 6,013,122 A | 1/2000 | Klitzman et al. |
| 6,207,874 B1 | 3/2001 | Felton et al. |
| 6,208,749 B1 | 3/2001 | Gutkowicz-Krusin et al. |
| 6,299,307 B1 | 10/2001 | Oltean et al. |
| 6,341,831 B1 | 1/2002 | Weber et al. |
| 6,470,891 B2 | 10/2002 | Carroll |
| 6,550,356 B1 | 4/2003 | Underwood |
| 6,800,122 B2 | 10/2004 | Anderson et al. |
| 6,890,319 B1 | 5/2005 | Crocker |
| 7,024,033 B2 | 4/2006 | Li et al. |
| 7,207,242 B1 | 4/2007 | Daigle |
| 7,249,712 B2 | 7/2007 | Ingalls |
| 7,344,587 B2 | 3/2008 | Khan et al. |
| 7,510,603 B2 | 3/2009 | Michel |
| 7,634,142 B1 | 12/2009 | Bourdev et al. |
| 7,738,032 B2 | 6/2010 | Kollias et al. |
| 7,922,688 B2 | 4/2011 | Bodduluri et al. |
| 7,945,302 B2 | 5/2011 | McAdams |
| 8,036,448 B2 | 10/2011 | Gildenberg |
| 8,083,422 B1 | 12/2011 | Simmons et al. |
| 8,090,224 B2 | 1/2012 | Lapstun et al. |
| 8,189,905 B2 | 5/2012 | Eaton et al. |
| 8,452,778 B1 | 5/2013 | Song et al. |
| 8,679,096 B2 | 3/2014 | Farritor et al. |
| 8,811,680 B2 | 8/2014 | Takiguchi |
| 8,819,024 B1 | 8/2014 | Toderici et al. |
| 9,022,949 B2 | 5/2015 | Herndon |
| 9,087,297 B1 | 7/2015 | Filippova et al. |
| 9,364,171 B2 | 6/2016 | Harris et al. |
| 9,371,957 B2 | 6/2016 | Dallarosa |
| 9,445,087 B2 | 9/2016 | Hillebrand et al. |
| 9,452,281 B2 | 9/2016 | Chan et al. |
| 9,486,290 B2 | 11/2016 | Zingaretti et al. |
| 9,505,134 B2 | 11/2016 | Guo et al. |
| 9,589,190 B2 | 3/2017 | Ramakrishnan et al. |
| 9,772,270 B2 | 9/2017 | Hyde et al. |
| 10,052,469 B2 | 8/2018 | Chan et al. |
| 10,130,260 B2 | 11/2018 | Patwardhan |
| 10,198,821 B2 | 2/2019 | Hougen et al. |
| 10,229,322 B2 | 3/2019 | Fridental et al. |
| 10,455,808 B1 | 10/2019 | Heath et al. |
| 10,692,220 B2 | 6/2020 | Gao et al. |
| 10,799,129 B2 | 10/2020 | Shiono et al. |
| 11,058,857 B2 | 7/2021 | Brown |
| 11,547,841 B2 | 1/2023 | Azdoud et al. |
| 11,839,734 B2 | 12/2023 | Azdoud et al. |
| 11,890,441 B2 | 2/2024 | Azdoud et al. |
| 2002/0110672 A1 | 8/2002 | Muratore-Pallatino |
| 2003/0095582 A1 | 5/2003 | Ackley |
| 2004/0146290 A1 | 7/2004 | Kollias et al. |
| 2004/0267121 A1 | 12/2004 | Sarvazyan et al. |
| 2005/0172852 A1 | 8/2005 | Anderson et al. |
| 2005/0234751 A1 | 10/2005 | Ingalls |
| 2007/0004972 A1 | 1/2007 | Cole et al. |
| 2007/0006497 A1 | 1/2007 | Alberts |
| 2007/0032846 A1 | 2/2007 | Ferren et al. |
| 2007/0060867 A1 | 3/2007 | Xu |
| 2008/0027279 A1 | 1/2008 | El Kheir |
| 2008/0033356 A1 | 2/2008 | Kluge et al. |
| 2008/0039827 A1 | 2/2008 | Ferren et al. |
| 2008/0078271 A1 | 4/2008 | Atkinson |
| 2008/0195043 A1 | 8/2008 | Schwach et al. |
| 2008/0208236 A1 | 8/2008 | Hobbs et al. |
| 2008/0214987 A1 | 9/2008 | Xu |
| 2008/0247637 A1* | 10/2008 | Gildenberg ............ A61B 34/70 901/41 |
| 2008/0273748 A1 | 11/2008 | Meiring et al. |
| 2008/0300615 A1 | 12/2008 | Colton et al. |
| 2009/0000513 A1 | 1/2009 | Michel |
| 2009/0183602 A1 | 7/2009 | Crockett |
| 2009/0227994 A1 | 9/2009 | Grundfest et al. |
| 2010/0030111 A1 | 2/2010 | Perriere |
| 2010/0245823 A1 | 9/2010 | Chhibber et al. |
| 2011/0148132 A1 | 6/2011 | Park et al. |
| 2011/0230833 A1 | 9/2011 | Landman et al. |
| 2011/0242132 A1 | 10/2011 | Bailey et al. |
| 2011/0246878 A1 | 10/2011 | Dowdell |
| 2011/0272976 A1 | 11/2011 | Wei |
| 2011/0288575 A1 | 11/2011 | Colton et al. |
| 2012/0040314 A1 | 2/2012 | Rubino, Jr. |
| 2012/0192681 A1 | 8/2012 | Klebs et al. |
| 2012/0300050 A1 | 11/2012 | Korichi et al. |
| 2013/0046324 A1 | 2/2013 | Williams |
| 2013/0098265 A1 | 4/2013 | Story et al. |
| 2013/0278716 A1 | 10/2013 | Kennedy et al. |
| 2014/0324089 A1 | 10/2014 | Chan et al. |
| 2016/0030134 A1 | 2/2016 | Shapter et al. |
| 2016/0067739 A1 | 3/2016 | Jones |
| 2016/0324586 A1 | 11/2016 | Zingaretti et al. |
| 2016/0328644 A1 | 11/2016 | Lin et al. |
| 2017/0259599 A1 | 9/2017 | Shinoda |
| 2018/0000419 A1 | 1/2018 | Rassman |
| 2018/0147400 A1 | 5/2018 | Brown |
| 2018/0177992 A1 | 6/2018 | Smith |
| 2018/0361589 A1 | 12/2018 | Paquin et al. |
| 2019/0294924 A1 | 9/2019 | Gould et al. |
| 2020/0311945 A1 | 10/2020 | Lim |
| 2020/0376855 A1 | 12/2020 | Lee et al. |
| 2020/0398036 A1 | 12/2020 | Wittendorff et al. |
| 2021/0060325 A1 | 3/2021 | Xiao |
| 2021/0256070 A1* | 8/2021 | Tran ................. G06F 16/90332 |
| 2021/0386987 A1 | 12/2021 | Azdoud et al. |
| 2022/0152371 A1 | 5/2022 | Azdoud et al. |
| 2022/0323736 A1 | 10/2022 | Asdoud et al. |
| 2022/0370778 A1 | 11/2022 | Azdoud et al. |

FOREIGN PATENT DOCUMENTS

| | | |
|---|---|---|
| WO | 2016109746 | 7/2016 |
| WO | 2018073439 | 4/2018 |
| WO | 2020178818 | 9/2020 |
| WO | 2021016590 | 1/2021 |

OTHER PUBLICATIONS

U.S. Appl. No. 62/813,085, filed Mar. 3, 2019, 34 pages.

ISA: United States Patent and Trademark Office, International Search Report and Written Opinion, PCT Patent Application No. PCT/US2022/013691, mailed Jun. 6, 2022, 14 pages.

* cited by examiner

ROBOTIC TATTOOING MACHINE WITH AN OPTICAL TATTOO ANALYZER TO ANALYZE TATTOOS ASSOCIATED WITH NON-FUNGIBLE TOKENS

CROSS-REFERENCE TO RELATED APPLICATION

The present application claims the benefit of U.S. Provisional Patent Application No. 63/192,534, filed Apr. May 24, 2021, entitled NON-FUNGIBLE TOKENS AND ASSOCIATED TECHNOLOGY, which is incorporated by reference herein in its entirety.

TECHNICAL FIELD

This invention generally relates to robotic tattooing apparatus, and more particularly, to applying tattoos using non-fungible token technology and associated technology.

BACKGROUND

To apply a tattoo, a handheld tattooing device vibrates a needle to inject pigment into the skin of a subject. If the injection is too deep, it may have a different hue due to scattering or may look blurred due to subdermal diffusion. If it is too superficial, it may not be held in proper position and may migrate to produce a blurred image or be gradually removed to produce a faded image as the dermis is recycled. Unfortunately, artistic ability varies between tattoo artists, and a particular tattoo artist may be unable to apply visually appealing tattoos. Tattoo artists may develop an expertise applying particular types of tattoos, such as micro tattoos, dotwork, blackwork tattoos, realism tattoos, or fine-line tattoos. An individual may want a tattoo that cannot be produced by a local tattoo artist, so the individual may travel to visit tattoo artists at other locations. In-demand tattoo artists often have exceptional skill that cannot be adequately replicated by other tattoo artists, so they may require booking weeks, months, or years in advance and the tattoos can be expensive. Additionally, people are unable to obtain authenticated tattoos of artwork from tattoo artists. Accordingly, conventional tattooing equipment and techniques have numerous drawbacks.

BRIEF DESCRIPTION OF THE DRAWINGS

The patent or application file contains at least one drawing and/or photograph executed in color. Copies of this patent or patent application publication with color drawing(s) and/or photograph(s) will be provided by the Office upon request and payment of the necessary fee.

Exemplary embodiments of the invention will be best understood by reference to the drawings, wherein like parts are designated by like numerals throughout. It will be readily understood that embodiments, features, and the components of the invention are generally described and illustrated in the figures.

DETAILED DESCRIPTION

Figure 1A:
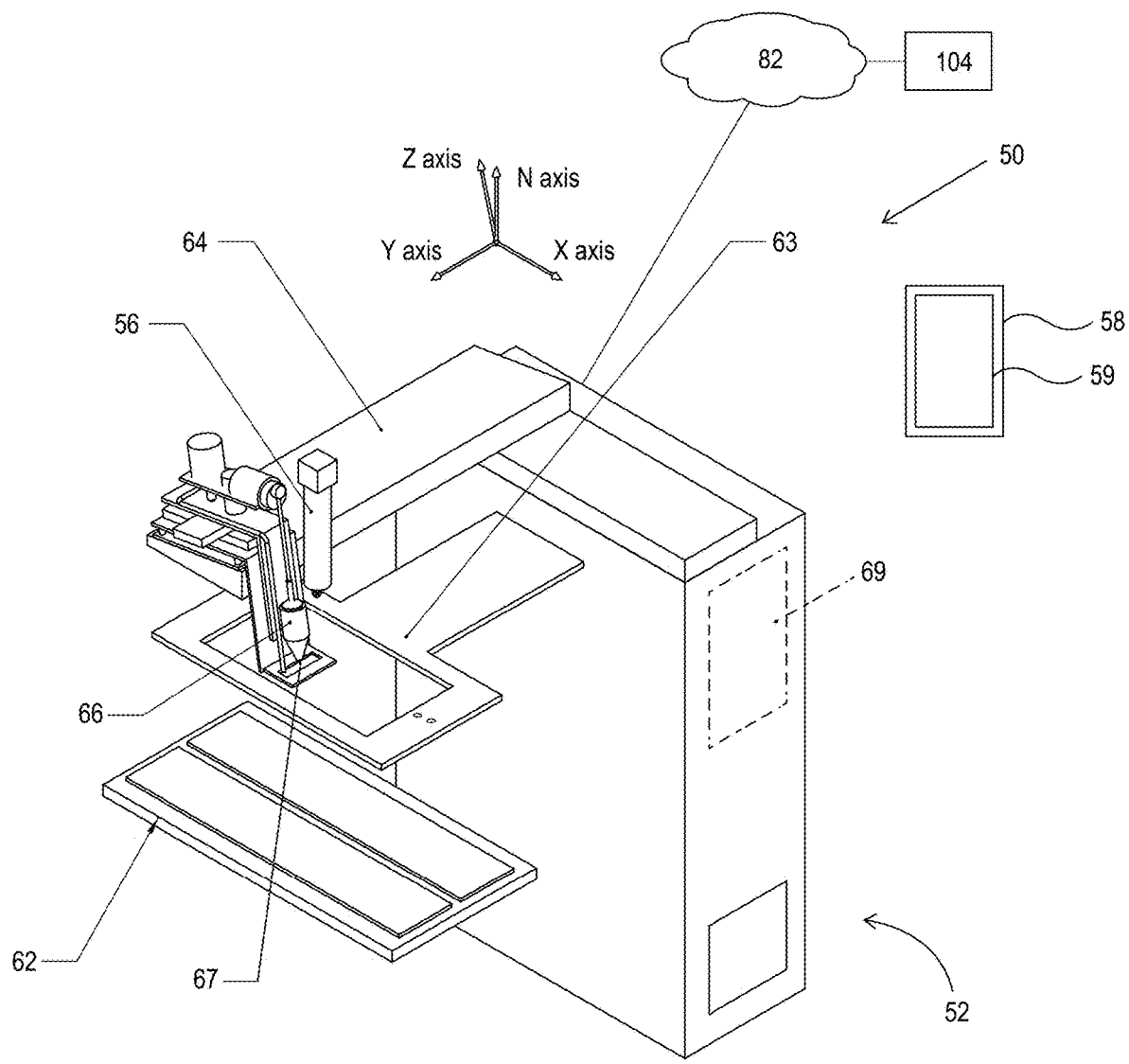
FIG. 1A illustrates a robotic tattooing system for applying authenticated artwork, in accordance with one or more embodiments of the present technology.

FIG. 1A is a schematic isometric view of a tattooing system 50, in accordance with one or more embodiments of the present technology. The tattooing system 50 can robotically apply artwork from digital marketplaces and includes a robotic tattoo machine or apparatus 52 and at least one controller 58. The controller 58 can determine a tattoo protocol or receive a tattoo protocol for applying artwork to subject's body part resting on a support surface 62. The tattooing system 50 can then tattoo the body part according to the tattoo protocol and includes an optical tattoo analyzer 56 that analyzes the tattoo (e.g., partially or completely applied) to determine, for example, whether the tattoo, or portion thereof, has been properly applied. The tattooing apparatus 52 can automatically authenticate the applied tattoo by performing, for example, one or more authentication routines. The tattooing system 50 can transmit the authentication to, for example, a digital marketplace (e.g., digital marketplace 104), user account, artist account, and/or another server or database or by operating a function in a smart contract.

The tattoo system 50 can reproduce artwork more consistently than a human tattoo artist such that individuals across the world can purchase artwork form an artist and receive a tattoo of the artwork without requiring that the individual travel to the artist. The tattoo system 50 can replicate tattoos from an in-demand tattoo artist without requiring booking with that artist, thereby reducing the time to receive the tattoo and costs. Artist-issued tokens can be used to limit, track, and manage the application of artwork. For example, the tattoo system 50 can apply, for example, micro tattoos, dotwork, blackwork tattoos, realism tattoos, and/or fine-line tattoos. In some embodiments, the tattoos can include one or more machine-readable identification features for identification (e.g., subject identification, tattoo machine identification, etc.), authentication, or the like.

With continued reference to FIG. 1A, the tattooing apparatus 52 may include a tattoo frame 63, and a tattoo shuttle 64 configured to carry a tattoo needle. The tattoo apparatus 52 can move the tattoo shuttle 64 while the tattoo frame 63 is held against the target tattoo site. The tattooing apparatus 52 can also include one or more sensors 66 and at least one controller 69. The tattoo device includes one or more needles 67 for applying ink and sensors 66 for measuring at least one characteristic of a subject's skin. The tattooing process can be controlled based at least in part on the measured characteristic(s) of the portion of skin, such as skin elasticity, impedance, or thickness (including thicknesses of one or more skin layers). The optical tattoo analyzer 56 can capture digital images of the skin to correlate the measured characteristic(s) of the portion of skin and the tattooing process. This data (e.g., near real-time data and/or real-time data) can be used to modify or generate tattoo command instructions for applying artwork.

The tattooing apparatus 52 can include a shuttle 64 configured to move the tattoo needle 67 along the subject. The actuator assembly 64 can include one or more motors (e.g., drive motors, stepper motors, etc.), robotic arms (e.g., multi-axis arms), gantry devices, linear slides, rails, sensors (e.g., position sensors, accelerometers, etc.), motors, rails, or the like. The tattoo apparatus 52 can be actuated along an axis, illustrated as an X axis. The X gantry may be a mechanical gantry that moves on the X axis and connects the tattoo shuttle to the cantilevered tattoo machine. A Y axis may be orthogonal to the X axis in a plane of the tattoo frame. An N axis may be normal to a plane formed by the X and Y axes. A Z axis may be formed with a degree of inclination relative to the N axis. In one embodiment, the Z axis is not orthogonal to the plane formed by the X and Y axes. For example, the Z axis may have a 10 degree, 15 degree, or 20 degree inclination to the XY normal (N axis) in the XZ plane, and 0-degrees in the YZ plane. In another example, the Z axis may have more or less than a 15-degree inclination in the XZ plane, and more or less than about 0-degrees in the YZ plane. In another embodiment, the Z axis is orthogonal to the plane formed by the X and Y axes. The controller 69 can be a computing device with one or more displays for displaying artwork, tattoo designs, stenciling, tattoo needle paths, tattoo session information (e.g., length of session, costs, color of inks to be applied, etc.), and/or visualization of artwork to be applied. In some embodiments, the controller 58 (e.g., a portable controller) can include a display 59 that can provide visualization of artwork selected by the client. The client can input location information such that the system virtually applies the tattoo using augmented reality or other visualization techniques. A user can specify a location by overlaying an image of the design on an image of their skin (e.g., via a live feed from their camera, a previously captured image, etc.). The system can then use computer vision techniques to identify position and orientation of the design in relation to, for example, the body party and/or one or more skin features, such as existing tattoos, moles, hairs, wrinkles, blemishes, etc. The position and orientation of the design, in relation to these skin features, can then be stored (e.g., stored by controllers 58 and/or 69), allowing the tattooing system 50 to recognize these skin features and apply the selected design with the same position and orientation characteristics.

If a color tattoo is applied, the tattooing system 50 can automatically select recommended colors based on the tattoo design, skin characteristics (e.g., skin color, skin tone, etc.), and/or other tattoo parameters. For example, the tattooing system 50 can have a pre-determined mapping of skin characteristics to preferred or undesirable tattoo characteristics that it can use to make suggestions when a user identified to have such a skin characteristic selects a design with undesirable tattoo characteristics or without preferred tattoo characteristics. In some implementations, this mapping can include corrective measures, such as a change in color or tattoo position when such a suggestion is made. The client and/or operator can select the size the tattoo, color the tattoo, place in the tattoo, and/or parameters based on the displayed information. The display 59 can be a touchscreen to enable convenient input. A stencil can be applied to the customer to review the design's positioning on the skin before starting the tattooing operation. Positioning of the design and/or stencil may also be reviewed using augmented reality. In some embodiments, a final tattoo design can be overlaid on a camera image or live video, based on the positioning and deformation of the applied stencil on the image detected by machine vision.

The tattooing system 50 can be used to apply artwork associated with distributed ledgers. The tattooing system 50 can include a network 82 for communications between the tattooing apparatus 52 and the digital marketplace 104. International Patent Application No. PCT/US2020/043588, International Patent Application No. PCT/US22/13691; U.S. application Ser. No. 17/584,011; and U.S. application Ser. No. 17/157,935 disclose digital marketplaces, tattoo machines, and systems and components that can be part of environments with distributed ledgers, including distributed ledgers for tokens. For example, the tattooing system 50 can be part of a token-based marketplace discussed in connection with FIG. 1D. In some embodiments, the tattoo machine 52 can perform one or more of the steps discussed in connection with FIG. 4. For example, the tattoo machine 52 can perform all of some of the steps discussed in connection with the tattoo machine 470 of FIG. 4.

Figure 1B:
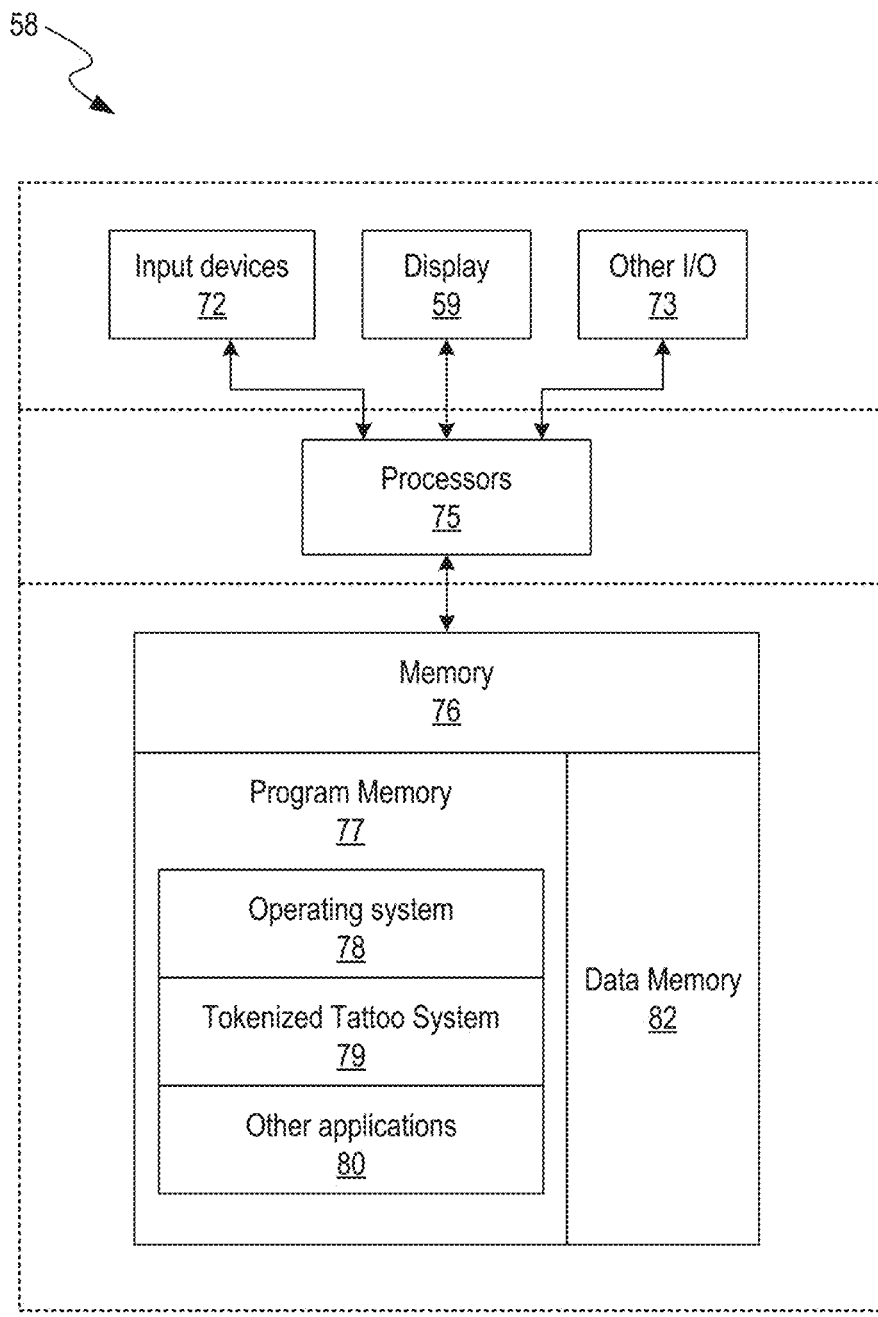
FIG. 1B is a block diagram illustrating an overview of a device, such as a portable controller, on which some implementations of the disclosed technology can operate, in accordance with one or more embodiments of the present technology.

Several implementations are discussed below in more detail in reference to the figures. FIG. 1B is a block diagram illustrating an overview of a device 58 (e.g. a controller) on which some implementations of the disclosed technology can operate. The devices can comprise hardware components of a device 58 that can create, image, analyze, manage, and delegate artwork, digital token, user account information, etc. by a user (e.g., a recipient of a tattoo, tattoo artist, operator of automated tattooing machine, etc.). In some embodiments, such a device 58 may permits the operation of an application on the display 59 of FIGS. 1A and 1C for the visualization of artwork to be applied on skin and which can recognize and authenticate existing tattoos applied on skin and their owners. Device 58 can include one or more input devices 72 that provide input to the Processor(s) 75 (e.g., CPU(s), GPU(s), HPU(s), etc.), notifying it of actions. The actions can be mediated by a hardware controller that interprets the signals received from the input device and communicates the information to the processors 75 using a communication protocol. Input devices 72 include, for example, imagers (e.g., camera- or image-based input device), a touchscreen, an infrared sensor, a touchpad, a wearable input device, a, a microphone, a mouse, a keyboard, or the like. For example, the input device 72 can include one or more cameras configured to capture digital images of tattoos. The imagers used in this application may have high resolution for the imaging of features such as minute variation of skin textures (pixel images of the skin with resolution better than 5 μm/pixel), but could also be used for more gross imaging of the whole tattoo (image resolution between, for example, 50 μm/pixel and 1 mm/pixel). In some embodiments, the imagers may be used in pairs or in groups for stereoscopic imaging and may be used in concert with infrared light sources and infrared sensors for depth detection. During tattoo application, the imagers may be used to identify a tattoo seeker's skin to digitally project, through its user interface 91, augmented images of the skin by overlapping selected artwork.

Processors 75 can be a single processing unit or multiple processing units in a device or distributed across multiple devices. Processors 75 can be coupled to other hardware devices, for example, with the use of a bus, such as a PCI bus or SCSI bus. The processors 75 can communicate with a hardware controller for devices, such as for a display 59. Display 59 can be used to display text and graphics, graphical user interfaces, images (e.g., images of tattoos, artwork, etc.). In some implementations, display 59 provides graphical and textual visual feedback to a user. In some implementations, display 59 includes the input device as part of the display, such as when the input device is a touchscreen. In some implementations, the display is separate from the input device. Examples of display devices are: an LCD display screen, an LED display screen, a projected, holographic, or augmented reality display (such as a heads-up display device or a head-mounted device), and so on. Other I/O devices 73 can also be coupled to the processor, such as a network card, video card, audio card, USB, firewire or other external device, camera, printer, speakers, CD-ROM drive, DVD drive, disk drive, or Blu-Ray device.

In some implementations, the device 58 also includes a communication device capable of communicating wirelessly or wire-based with a network node. The communication device can communicate with another device or a server through a network using, for example, TCP/IP protocols. Device 58 can utilize the communication device to distribute operations across multiple network devices. Referring to FIGS. 1 and 2, for example, the device 58 can communicate the tattooing machine 52, network 82, server 104 and other components of the system 50.

Referring to FIG. 1B, the processors 75 can have access to a memory 76 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 76 can include program memory 77 that stores programs and software, such as an operating system 78, tokenized tattoo system 79, and other application programs 80. Memory 76 can also include data memory 82, e.g., data for creating and delegating tokens, managing tokens, associating tattoos with tokens/blockchains, managing digital wallets, configuration data, settings, user options or preferences, etc., which can be provided to the program memory 77 or any element of the device 58.

The tokenized tattoo system 79 can include machine-executable instructions for, for example, performing the methods discussed in connection with, for example, FIGS. 3, 6A and 6B. For example, the tokenized tattoo system 79 can include programs for performing image quality checks, image capture, NFT management (e.g., NFT identification, NFT authenticity scoring, NFT matching, user authorization protocols, or the like). The application programs 80 can include, for example, application programs for performing one or more steps discussed in connection with the methods of FIGS. 1D-6B. In some embodiments, the application program 80 can be configured to manage smart contract analysis, generation of tattoo instructions, manage payment processing, generate service consumption instructions, or other steps disclosed herein. The number and configuration of the programs can be selected based on the methods being performed by the system. In some embodiments, specific system and hardware resources may be operated for the interaction with tokenized tattoo through NFT in the blockchain, such as tamper resistant PUF (physical unclonable function) electronics for the storage and operation of private keys and signing blockchain transactions and messages. This may be operated by the tokenized tattoo system 79 for the identification of existing tattoo tokens in the blockchain. Other applications 80 may be used for visualization and image identification of tattoos.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like. The description of the device 58 can apply equally to the controller 69 of FIG. 1A and other computing devices disclosed herein.

Figure 1C:
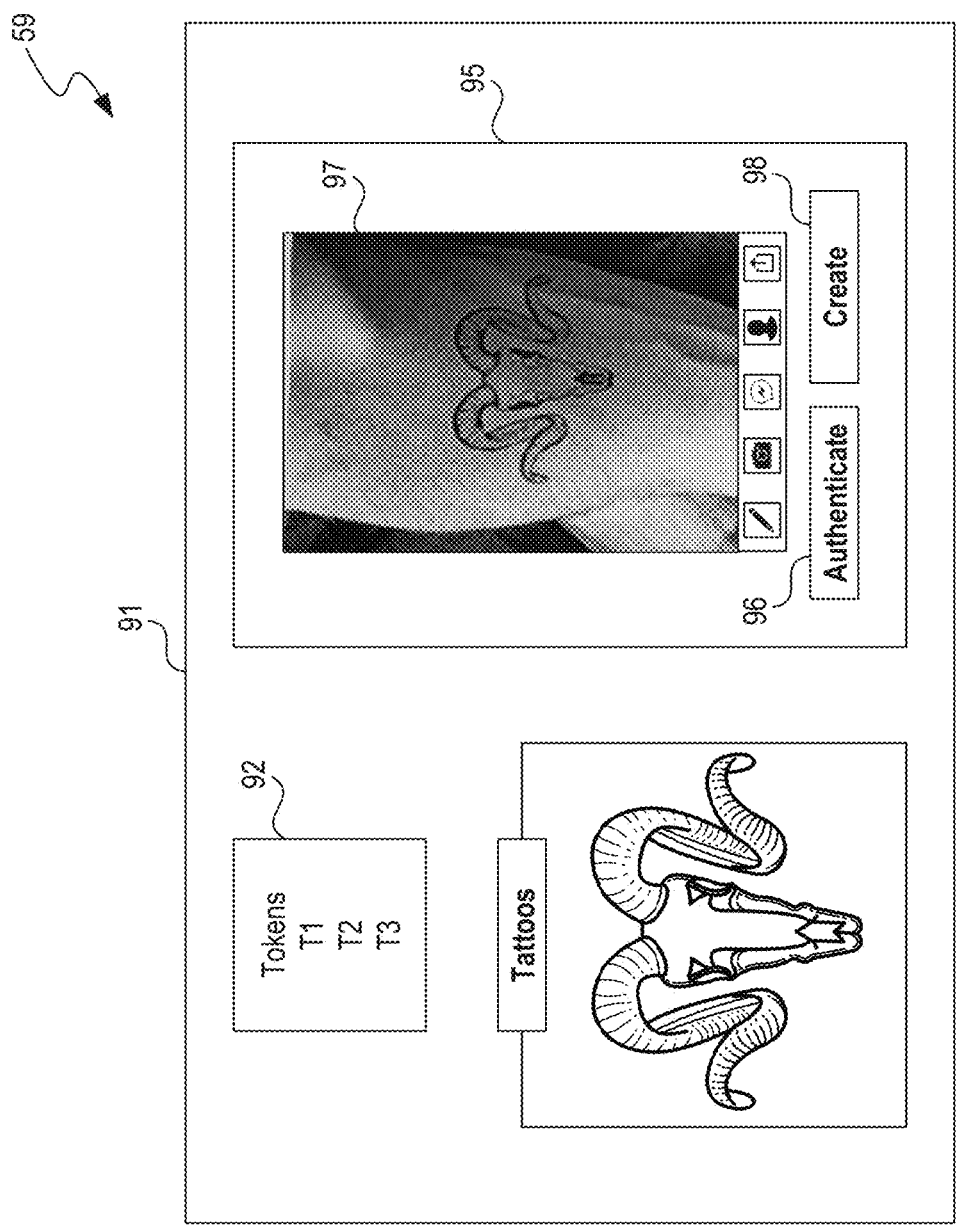
FIG. 1C illustrate an example of a user interface, such as the display of a controller 58 operating a visualization and certification application for the preparation of artwork to be applied as tattoo and for the authentication of ownership, in accordance with one or more embodiments of the present technology.
Figure 2:
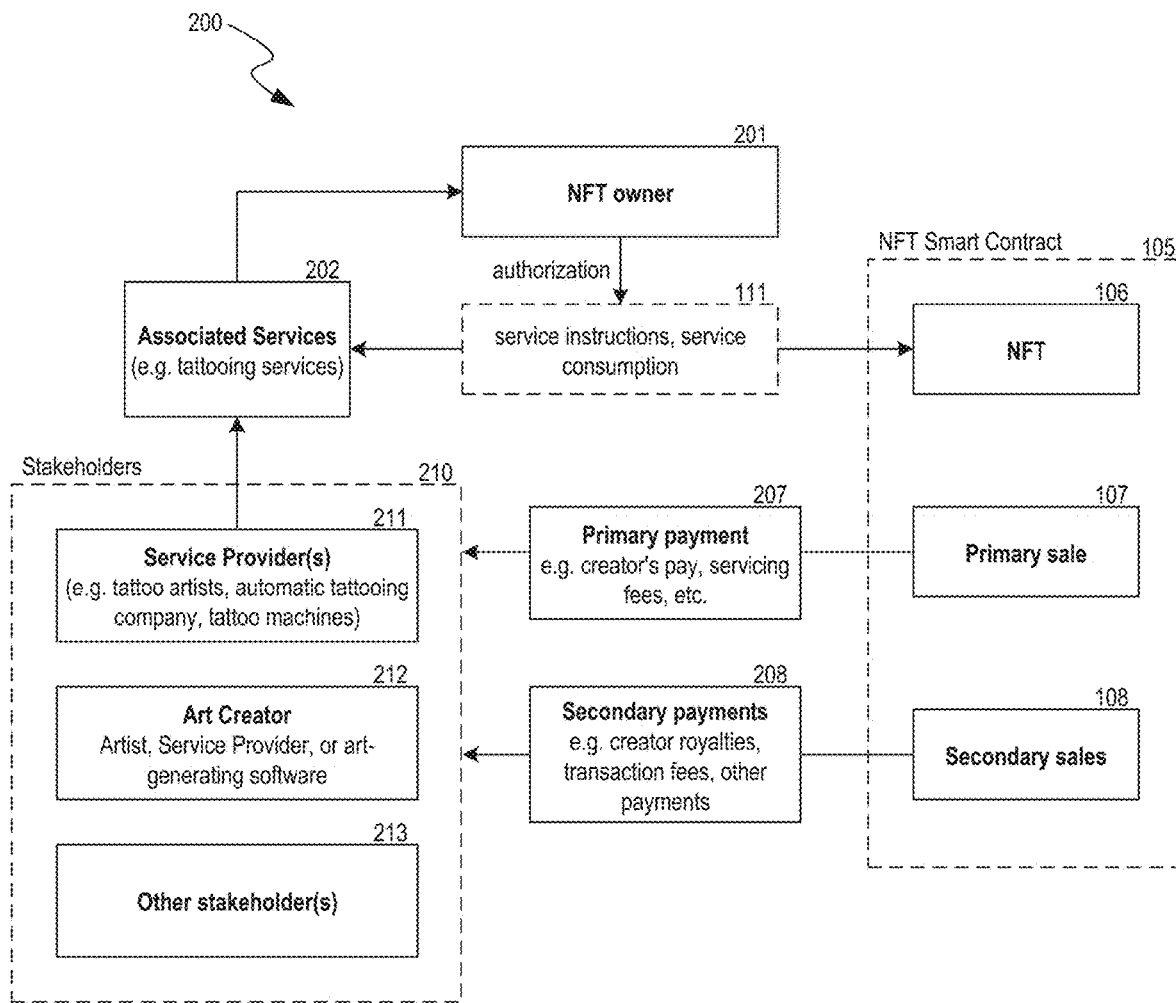
FIG. 2 is a flow diagram illustrating a process for payments related to the sales of NFTs and consumption of the associated services, in accordance with one or more embodiments of the present technology.

FIG. 1C illustrates an example device 59 with a user interface 91. The user interface 91 can include, without limitation, a digital wallet or token listing 92 with a list of tokens, a list of tattoos (one image of a ram's head illustrated), an authentication window/GUI 95. The list of tokens (e.g., T1-T3 in FIG. 1C) can include all tokens linked to the account of the token owner, who can select tokens from the list to view details on a currently selected asset in the window/GUI 95. The list 92 can indicate whether a tattoo associated with the token has been applied, whether a tattoo session has been scheduled for a token, etc. In some implementations, the owner can search the list for a particular item and select an item to view more details about the item in the currently selected window 95. These details can include current rights/capabilities associated with a token or an image. The window 95 can include authentication control button 96 for controlling, for example, imaging of a tattoo (e.g., capturing digital images of a tattoo), inputting digital signatures/identifiers, etc. The window/GUI 95 can show authentication data 97. The authentication data 97 can include, without limitation, one or more pictures (a picture of a ram's head tattoo is illustrated), videos, or other data for analyzing artwork, tattoos, or the like. In some implementations, the user can use a create button 98 input to generate tokens associated with artwork. The tattoos can be linked with the tokens in the list 92 upon authentication.

In some implementations, the user interface 91 can be used to manage tokenized tattoos. For example, a user can use the window/GUI 95 to analyze a tattoo (illustrated as a ram's head) on a body part. The user can use an image capture button (illustrated as a camera) to capture one or more images of the tattoo. The tokenized tattoo can be authenticated by selecting the authentication window 95. In some embodiments, the device can automatically scale and capture digital images of the applied tattoo to perform or start authentication routines. The tokenized tattoo can include or be associated with, without limitation, digital data (e.g., artwork, digital symbols, etc.), smart contracts, ledger addresses and information, or the like. A creator can use the create button 98 to create a token as described herein. In some embodiments, the window/GUI 95 can display token configurations and settings to allow the user to mint tokens. For example, the user can select a number of times that artwork is tattooed. In some embodiments, the user can use the user interface 91 to create non-fungible tokens.

The device 59 can process one or more tokenized tattoo system applications (e.g., tokenized tattoo system 79 and other applications 80 of FIG. 1B) to determine whether the tattoo has been applied. If the device 59 determines that a tattoo associated with one of the tokens 92 has been applied, the device can reject subsequent applications. In some implementations, the device 59 can analyze captured image data of a tattoo to determine whether the tattoo was applied using the tattoo instructions associated with a token. In other implementations, the device 59 can send image data to a remote server that performs one or more of the steps.

If the tokenized tattoo is applied during a tattoo session, the device 59 can transmit a communication to update a distributed ledger indicating that the tattoo was applied. In some embodiments, a smart contract associated with the tokenized tattoo can include a number of times a digital image is permitted to be applied. The device 59 can send a notification that one instance of that tattooing has been completed. The notification can be used to reduce the number of additional times the digital tattoo design can be applied. The token can be burned or its associated service fully consumed after the digital tattoo design has been applied the number of times permitted. In this manner, a creator of a token can set the number of times a digital tattoo design is applied.

Figure 1D:
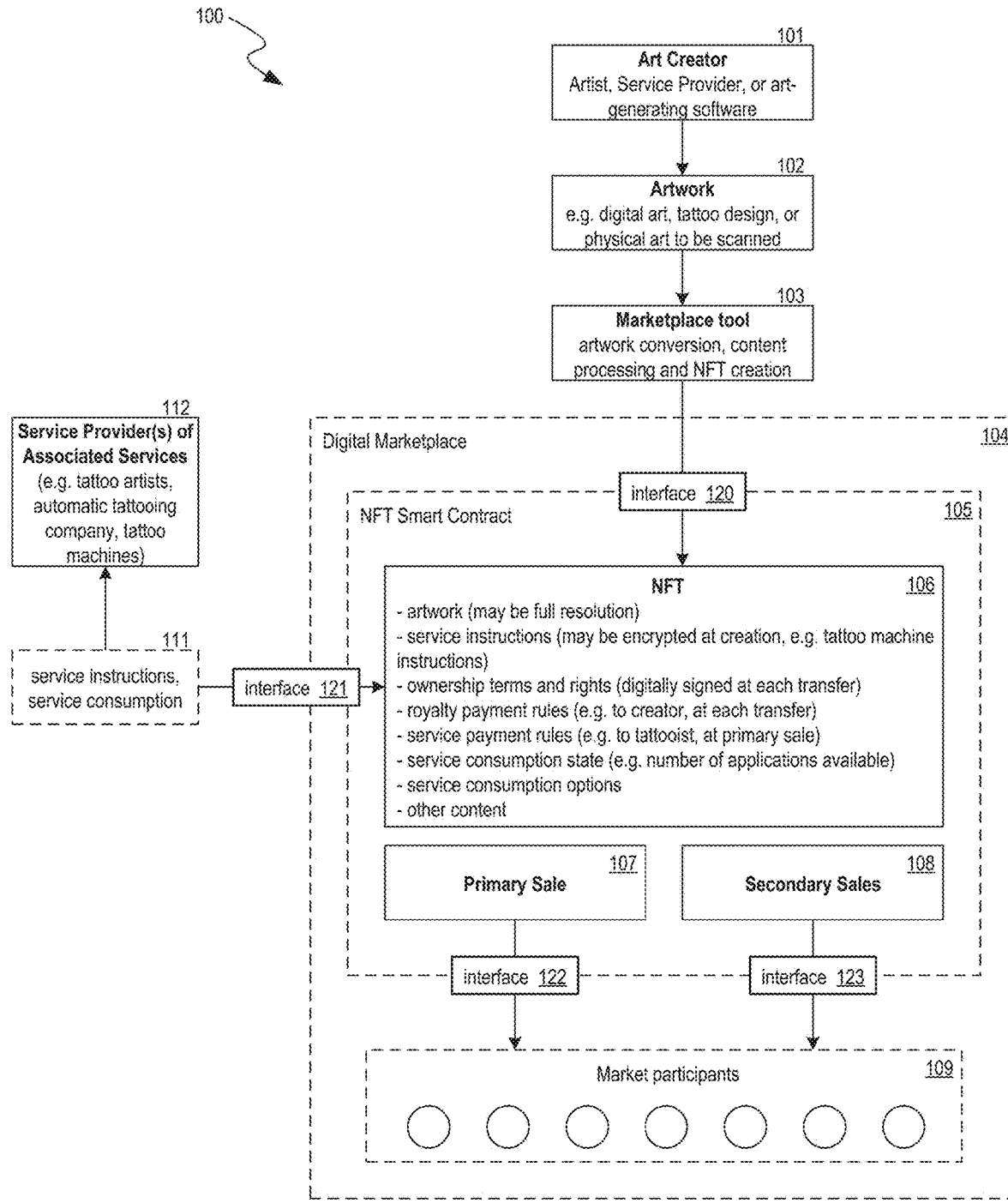
FIG. 1D illustrates an example of a token-based marketplace, in accordance with one or more embodiments of the present technology.
Figure 3:
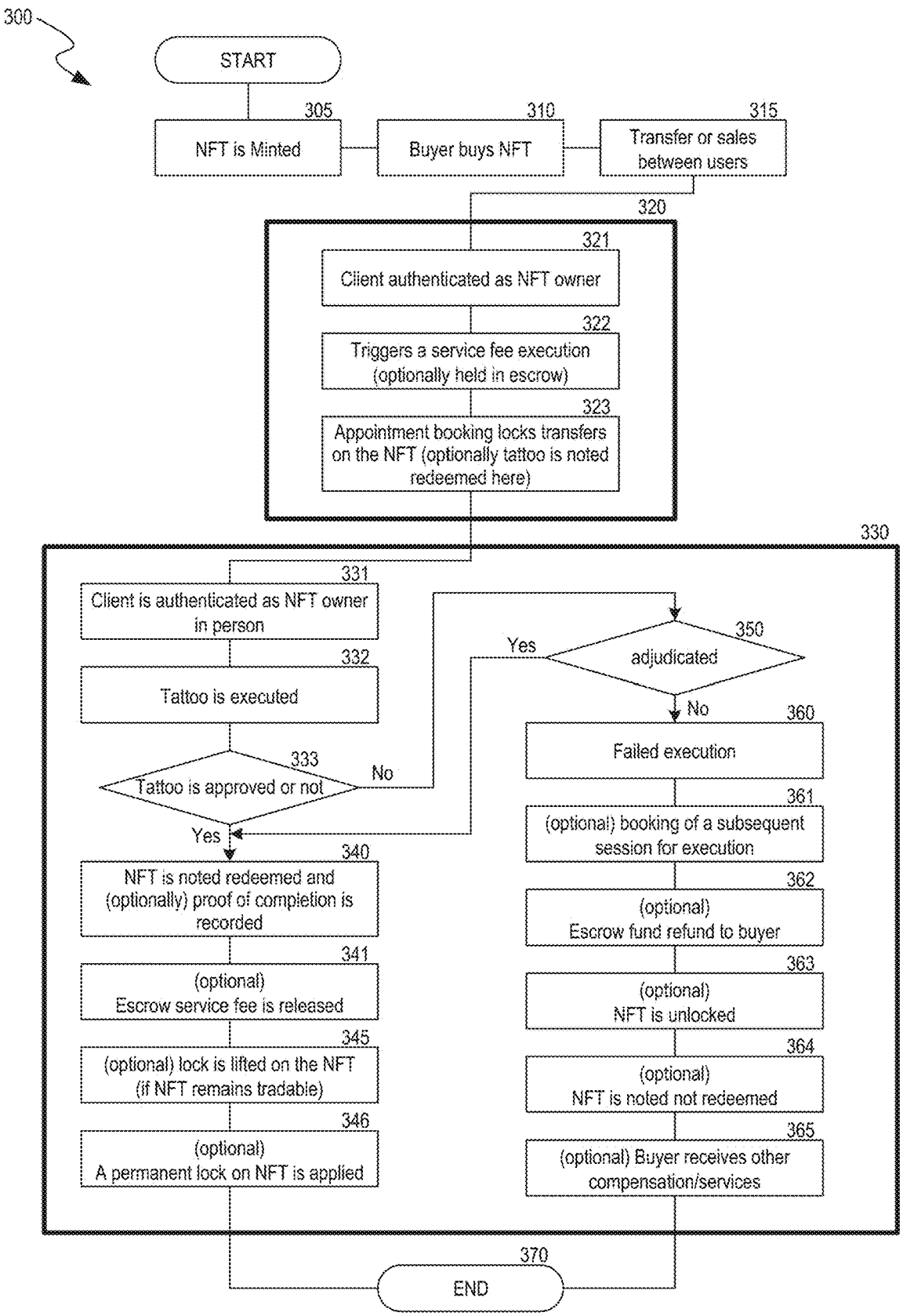
FIG. 3 is a flow diagram illustrating a process for booking and execution of a service associated with an NFT, in accordance with one or more embodiments of the present technology.
Figure 4:
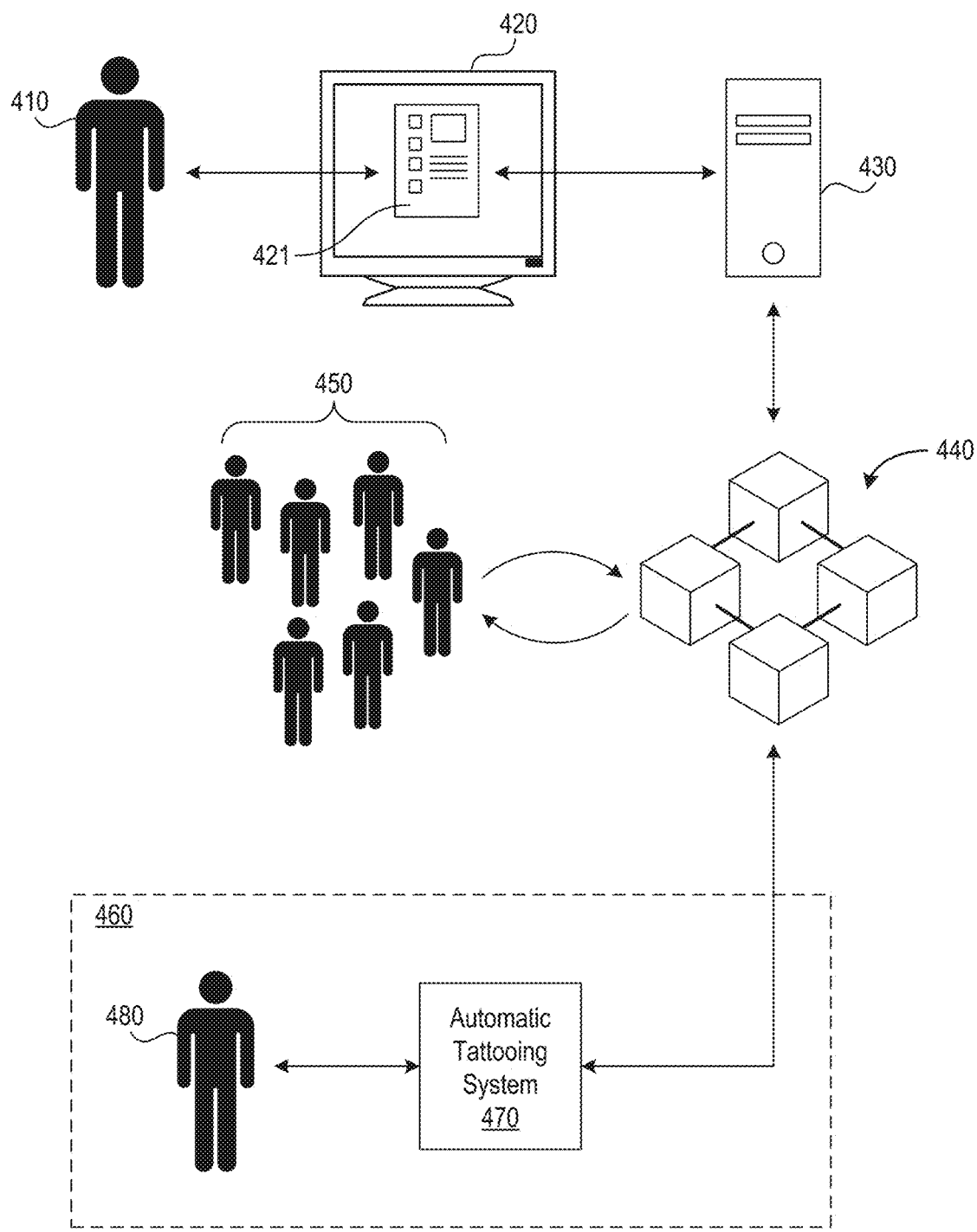
FIG. 4 is a flow diagram illustrating a process for creation, transfer and redemption of services associated with an NFT, in accordance with one or more embodiments of the present technology.

The user interface 91 can be used to perform other steps by interfaces disclosed herein, including interfaces 120-123 of FIG. 1D, interface 421 of FIG. 4, etc. The interfaces can have buttons, filters, windows, tools (e.g., image editing tools, digital wallet tools, ledger tools, etc.) to manage operations. For example, the user interface 91 can include an online/digital marketplace interface configured to allow a person to purchase and manage tokens. One example interface (e.g., interface 421) is discussed in connection with FIG. 4. The user interface 91 can be displayed on the device 59 of FIGS. 1A and 1C, a smartphone, a personal computing device, an on-board vehicle display, or the like. The user interface 91 can include blockchain information, a list rights associated with smart contracts, token information, etc. The user interface 91 can also be configured to track of methods disclosed herein, including methods discussed in connection with FIGS. 1D-6. For example, the user interface 91 can be used to manage tokens (Non-Fungible tokens), assets associated with distributed ledger smart contracts, digital wallets, access token-based marketplaces, etc.

Non-Fungible tokens (NFTs) are cryptographic, distributed ledger smart contracts with the specificity of using digital art as part of the token. Contrary to fungible tokens, each non-fungible token is unique. Art NFTs typically are associated with the ownership of the digital art. At least some embodiments are directed to assets (e.g., tangible and/or intangible assets) and services associated with the assets of the NFT and processes for creation and consumption of those assets. The assets can be artwork, such as digital artwork, stenciling, etc.

NFTs can be used in the field of tattooing to manage a tattoo client, art generation, art conversion into tattoo instructions, manage payment of stakeholders, allow a client to buy and sell tattoos in a secondary market, book/manage tattoo sessions, or combinations thereof. An NFT structure allows for the certification of ownership. For the context of tattooing, a smart contract may be used to track ownership of the digital design rendition of the tattoo and tattooing information, such as tattoo instructions, the tattoo design, metadata about stakeholders and licensing and royalty rights and, in the case of automatic tattooing, tattoo command instructions directly operational by an automated tattoo machine (e.g., tattooing apparatus 52 of FIG. 1A). Tattoo information and tattoo instruction may be stored in a database and the NFT may contain the hash of the tattoo instructions and information for the purpose of unique identification, as well as hyperlinks pointing to the database for retrieval. The NFT may contain the rights for the execution of the tattoo, which may allow one or many applications of a tattoo rendition of the NFT digital design, such right being consumed in the process of successive executions until the NFT may not contain any rights associated with tattooing. The smart contract can be used to support the sale or transfer of other cryptographic assets and their associated rights or services. The smart contract can be computer code used to implement transactions of a contract. The computer code can be executed in a secure platform that supports recording transactions in blockchains, ledgers, or the like.

For the purpose of creating, trading, and/or executing the rights of such NFTs, a digital marketplace has suitable tools for the creation, trade, and/or execution of tattoos. The marketplace may contain a tool for the creation of NFTs, where the digital design rendition of the tattoo and tattooing information such as tattoo instructions, the tattoo design, metadata about stakeholders and licensing and royalty rights and, in the case of automatic tattooing, tattoo command instruction directly operational by an automated tattoo machine may be specified and included prior to the NFT creation. The marketplace tool may automatize the generation of assets associated with the NFT. Once created, the NFT may be sold for primary or secondary sale through the marketplace trading tool, which may track and distribute appropriate transaction fee(s) and initial cost of the NFT, which may include the total or partial execution cost of the tattoo. Further, the NFTs associated services may be executed and the consumption tool may be used to file tattoo appointments and tattoo execution. The marketplace or NFT administrator may further modify or destroy the NFTs based on the consumption of some or all of the associated services.

The system can manage the creation and primary sale (e.g., initial offering in the NFT marketplace) of an NFT (e.g., NFT with assets and/or services derived from the art associated with the NFT). In some embodiments, the asset or service may be the execution of the digital art as a tattoo. The NFT can serve as the vector of associated assets or services which may be partially or fully compensated with the primary sale of the NFT. The assets or services may then be traded, alongside the NFT, on an NFT marketplace between various digital wallets, etc. In some embodiments, a transaction service fee for one or more trades may contain partial payment of, for example, royalty or additional profit associated with the asset, service or use of the digital art. Furthermore, in some embodiments, the transaction fee can be associated with a cryptographic token.

After the NFT is traded, for at least the primary sale, the associated asset or service can be redeemed. For example, in the context where the associated service is tattooing, a tattoo may be applied. In some embodiments, this tattoo may be a rendition of the digital art associated with or stored in the NFT. The NFT smart contract may contain one or more rules related to the consumption of the associated asset or service, such as: (1) the NFT may be destroyed with the consumption of its assets or services, therefore it cannot be further traded, (2) the NFT may outlive the consumption of the asset or service (e.g., the NFT can be modified such that already consumed assets or services is not possible) and/or (3) in the case the asset and service are consumed in their totality, the NFT may remain as a purely intangible token. For example, an NFT associated with the application of a tattoo may remain active and/or tradeable on the marketplace after the application of the tattoo, but may not allow further tattoo application.

In some embodiments, the NFT may contain or point toward instructions for the consumption of the asset and/or services. In some embodiments where tattooing is the associated service, the digital art associated with the NFT may be a direct representation of tattoo settings, such as ink dot position and depth, ink type and number of punctures associated with the execution of the tattoo as well as fiducial stenciling, in particular, for the robotic application of the tattoo art. In some embodiments, the digital art contained in the NFT may contain a direct representation of stencils, outline, guidelines, or other tattooing aids that may be used by tattoo artists for facilitating the tattooing process.

The systems can include a marketplace and methods which can be used for the creation, a primary sale (i.e., initial offering), secondary sale (i.e., subsequent sale(s) or trade(s) in the market place), and facilitating the consumption, modification or destruction of NFTs in the event of the consumption of its associated assets or services. In some tattooing embodiments, the system manages the creation, primary sales, secondary sale and consumption, modification and/or destruction of NFTs associated with a tattooing service.

FIG. 1D illustrates an example 100 of a token-based creation and sales of associated art and services, in accordance with one or more embodiments of the present technology. The creation of the NFT is associated with the creation of the digital art and metadata associated with this art (see, e.g., steps 101-106 in FIG. 1D). In the embodiment of a tattooing specific NFT, the digital art 102 may be a tattooable art or art that can be converted into a tattoo. In the embodiment associated with automatic tattooing, the digital art 102 may be a conversion of digital or physical art into a tattoo file. The tattoo file can contain execution information for the automatic tattooing, which may still be displayable as digital art. Additional metadata, such as machine settings or instructions, needle type, needle height, volume of ink, ink references and/or other settings associated with automatic execution of a tattoo may be attached to the digital art and associated with the NFT 106 at the time of creation. The metadata can include machine settings or instructions for different tattoo machines, including tattoo machines disclosed in International Patent Application No. PCT/US2020/043588, International Patent Application No. PCT/US22/13691; U.S. application Ser. No. 17/584,011; and/or U.S. application Ser. No. 17/157,935. In the embodiment associated with manual tattooing, the NFT 106 may point to additional aids for the execution of the tattoo, such as lists of inks to be used, needle types, machine types, stencils and outlines of the design and as well as a list of instructions for facilitating tattoo execution (e.g., by a tattoo artist).

An NFT may be created by converting this art and associated metadata and contract terms associated with the assets or services into metadata associated with the NFT stored in a database (e.g., through a file storage system like IPFS), hash of the data and hyperlinks included in an NFT, and added to the NFT blockchain or distributed ledger. The NFT may be created prior to its primary sale by various parties:

1. By the artist, to be submitted on the market for primary sale;
2. By the asset or service provider, to be submitted on the market for primary sale;
3. By the primary sale buyer or executor prior and in relation to the primary sale; and/or
4. By the marketplace authority after submission of art by artists and asset and service rights by asset and service providers, to be submitted on the market for primary sale.

The NFT creator can define the terms of the smart contract upon minting. In some embodiments, the NFT may be associated with a ledger, specific distributed cryptographic ledger on an existing blockchain, such as Ethereum, FLOW, Tezos, Polygon or Avalanche, or a new blockchain may be created for the purpose of tracking and authenticating ownership of the NFT and associated services. The associated blockchain standard may use, for example, proof of stake, proof of work, and/or another consensus mechanism and may contain one or more protocols to alter and/or destroy the NFT following the consumption of associated services or assets.

The creation of the NFT may be restricted to a specific marketplace 104 which may further limit the creation and original primary sale or subsequent sale of the NFT to transaction conducted through the marketplace.

The marketplace may facilitate the creation of the NFT governed by smart contracts 105 by automatizing the introduction of the art, the associated instructions for asset or service consumption and simplifying the publication for primary sale 107 and secondary sale(s) 108. In this context, the marketplace can take the form of a digital marketplace 104 with multiple client interfaces (120, 121, 122, and 123 in FIG. 1D) which may contain tools for the creation 103, primary sale 107, secondary sale 108 and consumption of associated assets and services 111. The client interfaces can be computing devices with screens displaying graphical user interfaces with the tools. In particular, in some embodiments related to automatic tattooing, the digital marketplace may be connected to a server controlling the automatic tattoo machines. FIG. 2 is a flow diagram illustrating a process 200 for payments related to the sales of NFTs and consumption of the associated services. In an embodiment of automatic tattooing, automatic tattoo machines may interact with the smart contract 105 (FIG. 2) to authorize and execute the tattooing service 202 associated with the NFT 106 and modify the NFT state to record the consumption event. Both (i) retrieval and decryption of the service instructions and the (ii) service consumption operations 111 may be performed digitally through authorization of the NFT owner 201.

In some embodiments related to automatic tattooing, the art alone may be uploaded as a digital or scanned physical art 102 (FIG. 1D) into the digital marketplace tool 103 that is responsible for NFT creation. This tool may proceed automatically to convert the art into tattooing instructions specific to the automatic execution of the tattoo, and publish the NFT 106 through the smart contract 105. In this process, the tool may prompt for review, modification, or edition of the art and NFT contract terms prior to NFT creation. In some embodiments, initial primary price may be specified by the user or may be calculated from the execution cost of the tattoo while generating the instruction for automatic execution, or a combination of thereof. For example, the tattoo execution cost may be calculated based on the estimated COGS associated with operating the machine which may depends on the tattoo size and number of dots, the cost of creation of the NFT, the applicable artist royalties and a user specified profit margin. The smart contract may be set up to automatically transfer appropriate portions of the primary sale proceeds (primary payment 207 in FIG. 2) to the wallets of the tattooing service provider 211, the art creator 212, and other stakeholder(s) 213. In one embodiment, the smart contract 105 may hold the price associated with tattoo application in a reserve, and transfer funds when the tattoo is applied. Similarly, in some embodiments related to manual tattooing, the NFT creation tool 103 may create or require instruction related to the application of the art such as stenciling, art outline, ink choice and needle choice that are recommended. In the case where the art is designed by the same individual that executes the art, some metadata about the studio were the tattoo may be subsequently executed may be listed as well.

When an NFT is created with associated services and assets that depend on the NFT associated art, information about the art creator and service or asset providers may be listed in the art metadata or smart contract variables so to track payment of royalties, service fees, asset payment or other form of payment to the art creator and service or asset providers during primary sale 107, secondary sale 108 and during consumption of the services or assets 111 associated with the NFT 106. This information may be added by the NFT creation tool of the digital marketplace. For example, in the case of a tattooing service, the tattoo art creator may be listed in the metadata or smart contract variables, in the form of an account or wallet, and the studio or studios or companies by which the tattoo can be redeemed in the form of an account, wallet, and/or studio location.

The creation of an NFT from a specific digital art may be delayed or duplicated. Multiple NFTs may be created related to a single piece of art. In the case of tattoos to be automatically tattooed, a specific tattoo may be part to a limited or unlimited series, for example one of ten. Therefore, for a single art piece, set of instructions and metadata, ten NFTs 106 may be created. The number of NFTs created for each art piece may be part of the smart contract 105 and may be authenticated by the NFT blockchain. For example, in a series of 1 of 10, 10 NFTs may be created from the same art piece. The NFTs created in that series of 10 may be created as a batch or created progressively at a time removed from the preparation of the art and other metadata in advance of NFT creation. The NFT creator can select the number of NFTs and how the NFTs are generated.

Similarly, an NFT may contain a single tattoo service or multiple tattooing services associated with artwork. For example, three tattoos of the same artwork may be performed from a single token. In the embodiment of automatic tattoo machines, the counter for the remaining number of applications may be decreased through the smart contract each time the tattoo is applied by a machine. Further, an NFT may be associated with multiple art pieces each containing a single service or multiple tattooing services. In some embodiments, an NFT can provide for multiple tattooing sessions for applying artwork. The NFT can be used for multiple tattooing sessions to apply large artwork to the same individual, multiple sessions (e.g., same artist or different artists) for applying the same artwork to different individuals, etc. In some embodiments, an NFT has, for example, multiple tattoo sessions associated with a single digital image. The primary purchaser can use one session to receive one tattoo and can then sell the remaining tattoo sessions on a secondary market.

The creation of the NFT containing associated assets and services may be limited to certain parties on the digital marketplace or centralized by a broker on the marketplace which validate the NFT creation and its addition to the blockchain. Once an NFT with the associated service and assets is created by the marketplace creation tool 103, it may be added to the blockchain and traded, either immediately or after a while, being published on the marketplace 104, for its primary sale 107. For example, an NFT may be created immediately prior to a primary sale, by finalizing the primary sale by creating the NFT when a wallet user selects prepared art on the platform. In another example, the primary sale may precede the creation of the NFT or the creation of the art and the NFT, such as in the case of a custom art piece.

The primary sale 107 may be performed after the creation of the NFT 106 and its submission to the marketplace 104. Primary sale can be made to a client who owns a cryptographic wallet. The wallet creation may be managed by the marketplace, where user can generate a cryptographic wallet to be registered as a marketplace participant 109. The user may then acquire a tattoo using currency in exchange with the NFT 106, acquired either in a primary or a secondary sale.

In the embodiment related to tattooing, the primary sale 107 (FIG. 2) includes cost of execution of the tattoo as well as art royalties and any other fees related to NFT creation, profit margin and so on. The payment of these fees to the stakeholders 210 may be executed at the NFT primary sale 107 or may be delayed, for example the payment of the tattoo execution may occur after the tattoo is executed. The NFT smart contract 105 contains the information necessary for the execution of fee payment, in particular the account information of all the stakeholders 210 involved in the transaction. The payment may be performed through digital currency such as a cryptographic currency specifically associated with the marketplace (a custom digital currency), or using fiducial currencies such as cryptographic (e.g., bitcoin) or national (e.g., dollar) currencies.

After its primary sale 107, the NFT ownership may be transferred between digital wallets on the cryptographic blockchain. The NFT associated assets or services may be readily consumed 111 or partially consumed and/or traded on the marketplace trading tool or interface 123. Trading of the NFT blockchain may be restricted to the marketplace it was created on. In the case of a trade listing, the NFT owner may submit a specific price at which the NFT is subjected for sale, setup an auction for a limited time and/or accept bids with a reserve price, and/or choose to receive unsolicited offers by third party wallet holders on the marketplace. The marketplace trading tool may suggest an estimated value of the NFT based on its associated services and assets, current valuation and rarity of the associated art. For example, in the case of tattooing, a tattoo that is in a limited series of 1 may have a higher suggested price when compared to a tattoo in a limited series of 10 or of an unlimited series.

The marketplace may list various NFTs that are for trade in its trading tool. These listings may contain and display pertinent information about each NFT. The listings may interpret the NFT to publish the associated art, its rarity, the number of listings of the same art currently on the market, the associated assets or services associated with the NFT, in order for buyers and sellers to evaluate the fair value and associated assets and services. Similarly, the Marketplace may allow digital wallet owners to display the information contained in the NFT.

Further, in some embodiments, the marketplace may offer fractional sale of an NFT, for example ⅓ or ¹⁄₁₀$^{th}$ of the NFT. In this instance, the associated assets and services may be partially consumable or not at all. For example, an NFT containing the right for 2 tattooing services associated with its art may be sold in four fractional parts. The ownership of one fraction of this NFT may carry the right for half a tattooing service, which is not sufficient for performing the tattoo associated with the art. The ownership of two fraction of this NFT carries the right for one tattooing service, which is sufficient for performing one tattooing service. Note that in the case of fractional NFT, the fraction may be restricted such as to maximize the consumption of the associated services and assets. For example, an NFT containing N services may have a number of fractions divisible by N such that 1/Nth of the NFT's ownership is sufficient to execute the service. Note that the fraction of an NFT is, in fact fungible, such that fractional NFTs are in fact semi-fungible. This means that a fraction of one NFT may not be interchangeable with the fraction of another NFT but may be interchangeable for the fraction of the same NFT.

In some instance, the NFT may be fractionable to the extent of its number of associated assets or services, for example an NFT containing the right for the application of N tattoos may be fractioned N times or a number M of times which is a divider of N (e.g., if N=4, M can be 1, 2 or 4).

If a secondary sale 108 is performed on the marketplace, the NFT or fractional NFT ownership is transferred from the seller's wallet to the buyer's wallet. The digital trade tool or interface 123 may charge a transaction fee. This transaction fee may include fees associated with royalties, and other fees 208 to the stakeholders 210 listed in the NFT smart contract, as well as processing fee associated with processing the trade, conversion of the art and/or taxes. The payment of these fees may be executed through cryptocurrencies or national currencies or a mix of both. In some embodiments, the transaction fees may be charged through a dedicated cryptocurrency associated with the marketplace. The transaction between buyer and seller may also be performed through cryptocurrencies and or national currencies, and the marketplace trade tool may include a currency conversion service which allow the buyer to pay in one currency and the seller may be paid in another currency through the currency conversion service.

All NFTs in the marketplace may be traded multiple times prior to any consumption of its associated assets and services 111. It may also be traded as part of the primary sale 107 before consumption or partially or totally consumed during its trades 108 on the marketplace. In some embodiments, the NFT is destroyed if all the assets and services associated with the NFT are consumed. In another embodiment, the NFT may still be traded 108 when its services are fully or partially consumed.

The described marketplace 104 can include a consumption tool or interface 121 for redeeming the assets and services associated with the NFT. The tool permits the certification of the modification or destruction of the NFT when its associated assets or services are partially or totally consumed. In the embodiment related to tattooing, the NFT tattooing service may be consumed 111 by the execution of a tattoo 202.

In an embodiment related to hand-made tattooing the certification process may be executed in a multipart process. Firstly, the NFT owner 201 (whose digital wallet contains the NFT 106) may schedule or list an appointment for the execution of the tattoo with the authorized tattoo artist. In some cases, the authorized tattoo artist is the designer of the original tattoo art that was used in the creation of the NFT. In other cases, the tattoo artist may be in a list of registered tattoo artists allowed to redeem the tattoos traded on the marketplace. In further other cases, the NFT owner 201 may select a third-party tattoo artist which is not on the platform. Once the tattoo is listed for execution, the associated NFT may not be traded with the associated tattoo execution service unless the tattoo was not applied. In some embodiments, the NFT may be blocked from being traded until the listed appointment is canceled or the tattoo is executed. This is done by modifying the NFT smart contract 105 by listing the tattoo execution as pending. In some embodiments, digital signature may be provided by the wallet owner to denote the start of the execution of the tattoo.

Secondly, the tattoo may be executed by the tattoo artist by accessing a specific tool or interface 121 on the marketplace dedicated to tattoo execution. In some embodiments, such a tool facilitates the display and access of the stored data within the NFT 106, such as allowing the printing of stencils, all the necessary tools checklist such as inks and needles, a progressive execution help by presenting the tattoo progress when going through the instruction list and recommendation related to proper execution of the tattoo 202. In some embodiments, the tattoo artist may need to provide a unique key or token, given by the marketplace or the NFT owner 201, prior to starting the tattooing process. The NFT owner may need to confirm tattooing execution start before tattooing is to start, to confirm the validity of execution.

Thirdly, proof of execution may be provided by, for example, the tattoo artist and/or the NFT owner. In some embodiments, a picture may be taken to show proof of execution after partial execution of the tattoo (if multiple sessions are necessary) and at complete execution of the tattoo. The picture may be used to verify that the execution of the tattoo was performed. The proof of execution can also be based on, for example, scans, video, still images, etc.

Fourthly, if the proof of execution is provided, the NFT 106 is further modified to destroy the associated service 202. The proof, such as pictures of the tattoo may further alter the NFT to denote execution. In some embodiments, the NFT 106 may be destroyed at this point or held by the marketplace 104 in storage in case of disagreement. In other embodiments, the NFT may still be traded on the marketplace by its owner, but with the associated consumed tattoo disabled for another application. In that case, any further trades 108 will not provide the new owner with an associated tattoo service 202, if such tattoo service was consumed at any point.

Fifthly, payment may be provided to the tattoo artist for the service. The fifth step may happen at different stages of the process, such as at the beginning, progressively during the execution or at the end.

This process may be different in embodiments associated with an automated tattoo machine operated by an authorized entity or by a marketplace service. Authentication and certification of the tattooing process may be guaranteed by machine-to-machine communication rather than through the intermediary of a tattoo artist. Unless stated otherwise in the following, the same process can be applied to hand-made tattooing.

Firstly, as for hand-made tattooing, the owner 201 of the wallet of an NFT may schedule an appointment for the execution of the tattoo through the marketplace for automated tattooing. The NFT may be suspended for trades 108 until the tattoo is executed or the tattoo session is canceled.

Secondly, the owner's wallet signature may be provided to the machine to communicate with the marketplace 104 and/or the smart contract 105 that the session is starting. The tattoo metadata and tattoo files may be transferred to the machine for the execution of the tattoo. In some embodiments, the tattoo art is converted into tattoo instruction just prior to the execution by the machine itself. Thirdly, proof of progressive execution is provided by the machine to the marketplace, such as machine logs and progressive images of completion. Fourthly, proof of completion is used to destroy the associated tattooing service from the NFT. Fifthly, payment for the service is processed.

In some situations, the execution of the tattooing process 202 may be incomplete, flawed, the tattoo was never executed, or there is a disagreement about execution. In such a case, the marketplace authority or NFT administrator may adjudicate to create a new token if it is deemed that the service execution was not performed. The initial value of this new token may be set by the marketplace authority or may be left to the wallet owner 201. The new NFT associated service or asset may or may not be traded in a secondary sale 108. For example, the new NFT may be designed specifically to complete or fix the execution of the incomplete, flawed, or unexecuted tattoo and may be untransferable to another wallet. In another situation, the owner of the NFT may not show up, or may cancel their appointment. A cancellation notice may be filed on the marketplace. A cancelation fee may be charged and the NFT limitation of trade with associated services may be lifted.

Once the service is consumed, such as in the execution of the tattoo is performed, the NFT may, in some instances, still be exchanged on the marketplace 104. In some embodiments, the NFT can be provided for robotic and/or manual tattooing. The user can choose how the tattoo is applied. If the user cannot travel to the artist, the tattoo can be applied locally by a robotic tattooing system, such as by the robotic tattooing systems disclosed in U.S. application Ser. No. 17/157,935. If the user can travel to the artist, the NFT can be destroyed or disabled when applied manually by the artist. In some embodiments, a portion of the tattoo can be applied robotically, and other portion(s) can be applied by one or more artist (e.g., collaborative tattooing).

In some embodiments, an automatic tattoo apparatus can be used to robotically apply tattoos associated with NFTs. A customer can shop on an online tattoo marketplace to select designs created by various artists located anywhere. The online tattoo marketplace can manage NTFs, payments, artist and/or customer profiles, bookings, tattoo design uploads, browsing and design selection, design changes, and/or perform other actions. The tattoo apparatus can apply a wide range of different types of tattoos, including but not limited to micro tattoos, dotwork, blackwork tattoos, realism tattoos, fine-line tattoos, etc.

The tattoo marketplace can supply the designated or recommended retail location for an NFT token (e.g., a digital token, credit, etc.) to receive a tattoo design. The online tattoo marketplace can be used to provide graphics and designs from tattoo artists, non-tattoo artists such as visual artists, artistic celebrities, influencers, brands, artwork provided by customers themselves, or other sources. This allows purchasers to access artwork irrespective of an artist's physical location. In some embodiments, the artist can receive payment based on royalties, commissions, or other payment schemes. The online tattoo marketplace can include original designs, limited edition designs, resident designs, custom lettering, custom designs, customer provided designs, or other designs. Additionally, the online tattoo marketplace may offer other goods and services including but not limited to NFT auctions, artwork auctions, or sale of NFTs. After the tattoo apparatus has applied the art, one or more pictures can be supplied to the marketplace, tagged to the artists/studio. The pictures can either be taken by the tattoo machine or by a mobile phone, tablet, or other image capture device of the tattoo recipient, artist, etc.

NFT Creation

FIG. 3 presents an embodiment of the invention related to the process 300 for booking and execution of a service associated with an NFT. In step 305, the NFT (106 in FIG. 1D) is created (or "minted") by interacting with the smart contract 105 on the blockchain 440 of FIG. 4. In this invention, minting of NFTs associated with tattoos or other redeemable services includes operations in addition to those described in, for example, ERC-721 standard, in order to enable functionalities related to redemption of services, mutual approval of services, copy-protection, copy-authentication, etc. In a preferred embodiment of the invention, the NFT is associated with a tattoo design and/or consumable tattooing services. In this embodiment, creation of the NFT 106 may be preceded by steps 101-103 discussed earlier in relation to FIG. 1D. Referring now to FIGS. 1D and 4, the minting of the NFT may be executed through an interface 120 (FIG. 1D), from an administrative address such as an approved operator, or in some embodiments directly by the buyer as a part of the primary sale 107 by sending a minimum required payment through the blockchain. In either case, a server 430 (FIG. 4) that is configured to interact with the blockchain 440 initiates function calls to the NFT smart contract 105 to create or "mint" NFTs. The minting process includes at least the functions designated by the ERC-721 standard, i.e. (i) creating a new cryptographic token and (ii) assigning the token's ownership to a wallet, which may be the buyer's (410 of FIG. 4) own wallet, or a wallet maintained by the NFT service provider to be stored until transfer to a first buyer 410. For example, a smart contract 105 function to mint an NFT may be:

_safeMint(address to, uint256 tokenId) internal
   _safeMint(address to, uint256 tokenId, bytes data) internal
     _mint(address to, uint256 tokenId) internal where "tokenId" is the NFT identifier and "to" is the recipient address of the token. The function exits operation if the address or the identifier is invalid. If both valid, a new token is created and transferred to the address "to". In addition, an externally-callable function may be implemented to allow mint requests:

mint(address to, uint256 tokenId) external payable

In order to mint a token, this function may require a payment above a minimum amount, or may require the function call to be made from an authorized administrator address. As specified by ERC-721, an externally-callable function tokenURI(uint256 tokenId) is implemented to query the URI of a token, which is a link to a file that contains additional data about the token. While a token's URI is typically set at the time of minting, it may be allowed to be adjusted to by an administrator address, to allow operations described in this invention (e.g. changing the displayed image of a tattoo after it is applied on skin). Tokens may be destroyed via the use of an internal function _burn(uint256 tokenId). In the context of NFTs representing tattoos, the burn function may be executed by the automatic tattooing system 470 (or 50 in FIG. 1A) after a tattoo is applied on the skin.

In order to enable the operations described in this invention, the NFT may also contain any of the following additional variables in memory for each token, along with the corresponding external functions to query them:

isTransferLocked: whether the token is locked for transfers isConsumed: whether service was consumed (single-consumption NFTs)

ConsumableCopies: number of copies available for consumption

ProofConsumed: hash of proof of consumption(s)

CopyPermitSignatures: digital signature(s) of copy permission certificates issued by the copyright holder (e.g. creator of the tattoo design)

CopyrightOwnerAddress: public address of the copyright holder

AmountServiceFeePaid: amount of pre-paid service fees

MinimumServiceFee: minimum service fee to execute services

In step 310 of FIG. 3, the NFT is purchased by the user 410 of FIG. 4. The purchase may be made by the user 410 on a computer or mobile device 420 through an online/digital marketplace interface 421 or 120, or in-person at a store (e.g., the service provider's store 460 or 112) through another interface. In either case, upon purchase of the NFT, the interface 421 or 120 submits the information to a server 430. The server 430 then initiates function calls to the NFT smart contract on the blockchain 440 to transfer the NFT to the buyer's wallet, in exchange of a payment. The payment may be made using conventional methods (online payments, credit card, bank, etc.), a blockchain payment, etc. In some embodiments, a dedicated smart contract (different than or similar to NFT smart contract 105) may be implemented on the blockchain to execute the initial sale, for example in the format of a fixed-price sale, or an auction. The payment may include ownership over the NFT, a certain number of copies of the service to be consumed and potentially prepayment for the booking and execution fee of the service. Other payments may be established for fees such as royalties, blockchain network fees, and taxes.

After the token is purchased by a user 410 (FIG. 4) in step 310 (FIG. 3), it may be transferred between the participants of a secondary market (450 in FIG. 4 or marketplace participants 109 in FIG. 1D) in step 315. The token may be transferred between wallets as a result of buying, selling, trading or gifting the tokens. The transfers between wallets are executed by making calls to the NFT smart contract 105 on the blockchain 440, using the following function specified on the ERC-721 standard:

function safeTransferFrom(address from, address to, uint256 tokenId, bytes data) external payable
function safeTransferFrom(address from, address to, uint256 tokenId) external payable
function transferFrom(address from, address to, uint256 tokenId) external payable The functions may be accessed via an interface 123, e.g., an app or software operating on a computer, tablet or a mobile phone. Optionally, the functions may be called by a smart contract governing a sale, auction, trade, or exchange on behalf of the market participants 109. These functions can behave the same as the original standard ERC-721 except that the functions interrupt operation if the token identified by "tokenId" is "locked" for transfers. Such transfer lock may be initiated in response to a specific stage of the service consumption (e.g., booking for redemption is made, services redeemed, etc.), and may be queried externally. The use case for transfer locks is described below in more detail.

In step 320 the owner of the NFT books an appointment with the service provider to redeem the services associated with the NFT. Information necessary to deliver the NFT-associated services (e.g. client information, tattoo execution date and time, delivery address for shipping associated products, payment information, etc.) are collected from the client and terms of sale or services may are displayed and agreed on.

In step 321 the user is verified to be the token owner. This is done by the user cryptographically signing a system-generated message with the private key of his/her wallet, proving wallet ownership. This step may be done through the wallet interface/API on a web browser. The smart contract is then queried by the ERC-721 standard function ownerOf(uint256 tokenId) to verify that the token to be redeemed belongs to the user's wallet. At this point, the service provider 112 knows the token owner shows an intent to redeem the NFT as a tattoo. The user, who is the current token owner verified at step 321, may be the first buyer (410) who obtained the token by the primary sale 107, or a secondary market participant (450 or 109) who obtained the token by a secondary sale 108.

Next in the booking process, the identity and payment information of the user may be collected by the service provider 112 and added to the appointment data along with the wallet and token id. The identity may be used to verify the person 480 at the service provider's store 460 by a government-issued/official ID. In tattooing services, checking user ID may be necessary to ensure the tattoo recipient is not under-age to receive a tattoo. Alternatively, collection of any personal information may be postponed until the in-person appointment 460, where an authentication step is performed (step 331 of execution).

At step 322 of the booking, fees or deposits are paid for the services to be executed by the service provider 112. The payment may be made using conventional methods (online payments, credit card, bank, etc.) or as a blockchain payment. If payment is made through the blockchain, then a blockchain escrow system may be used to release the funds to the service provider, upon acceptable execution of the services (described later in steps 341 and 362). Part of the payment may be non-refundable to protect the service provider from costs of a potential no-show. The execution fee may be paid entirely in person at store 460 of the service provider 112. The store 460 of the service provider 112 can include one or more robotic systems (e.g., robotic system 50 of FIG. 1A) for applying NFT tattoos, artists that manually apply the NFT tattoos, etc. In some hybrid tattoo session, a portion of a tattoo is applied robotically and another portion of the tattoo is applied manually. Agreements for terms of sale, or terms of service may also be digitally signed at this stage. Proof of digital signatures may be stored on- or off-block chain.

One embodiment of the invention is the modification of standard NFT smart contract to lock transfer of NFT in a temporary or permanent basis. The smart contract transfer lock, be it permanent or temporary, disables the ability to transfer the NFT to another user. In some embodiments of the invention the temporary smart contract transfer lock may be implemented when booking an appointment for the application of a tattoo associated with the NFT. This guarantees that the NFT does not transfer to another wallet in the interim between booking and redemption of the tattoo. The temporary smart contract transfer lock may be reverted by the booking service provider if the booking is canceled, or the tattoo is otherwise not applied or incorrectly applied. The temporary smart contract transfer lock may be initiated by the NFT owner, the service provider or by both. The temporary smart contract transfer lock may be ended by the service provider or by both the service provider and the NFT owner.

In some embodiment of the invention a permanent smart contract transfer lock may be implemented to be used as a consequence of the service being consumed, in particular when a tattoo is applied. The permanent transfer lock may be initiated by a service provider and may require proof of consumption of the service in the form of data provided by an automated tattoo machine and/or approval by the NFT owner. The permanent lock may or may not be initiated if a temporary lock exists. Transaction locks are implemented by a modification of the ERC-721 standard by the addition of a lock and associated function and events and the modification of the token transfer functions to authorize the transfer in instances where the lock is absent.

The following is an example of implementation of such methods for a locking system. The examples are presented using the syntax of Solidity scripting language, but any other language suitable for blockchain smart contracts may be used to implement the described functionalities. In this embodiment, the temporary lock is initiated solely by the owner of the NFT and is rescinded solely by the service provider. The permanent lock, through the function "consumeService" can solely be initiated if a temporary lock exists and by the service provider. A permanent lock may require data that provides proof of consumption. In some embodiment, the Permanent lock mechanism is not used and temporary lock are used, either for booking or for tattooing.

function temporaryLock(address_serviceProvider, uint256 tokenId)

This function initiates locking of transfer of an NFT. This function throws (i.e., exits with an error) if the NFT is already locked. This function throws if not redeemable. The function throws unless the caller of the function (msg.sender) is the current owner of the token (ownerOf (tokenId)) or an authorized address for the NFT. This function may throw if "_serviceProvider" is not an approved operator such as an approved service provider (112 or 460).

Event TemporaryLock(address_serviceProvider, uint256 tokenId);

This event emits when an NFT temporary lock is initiated.

Function isTransferLocked(uint256 tokenId) external view returns(bool)

This function returns a logical True if the queried NFT is locked and a logical False if it is not locked. This function does not distinguish between permanent or temporary transfer locks.

At step 323 in the booking process the NFT is locked for transfers by the booking system, by calling the temporary Lock function described above. Optionally, the NFT may be pre-maturely marked as redeemed at this step to reduce the number of blockchain interactions. The entire booking process 320 (steps 321-323) may be performed by the user on a personal device, or may be completed in-person at a service provider's store 460.

At step 330, services associated with the NFT are executed. In the case of tattooing, the client visits the tattoo studio in person to receive the tattoo on skin.

At step 331, the client is authenticated in-person as the owner of the NFT, at the location of the service execution (e.g., tattoo studio). The authentication step ensures the owner of the NFT is the person to receive the NFT-associated services. For tattooing, the client 480 appears in-person at the tattoo studio 460. In one embodiment, the in-person authentication is performed as follows. The service provider randomly-generates a verification code (e.g., a 6-digit number) and presents it to the client. The client then uses their cryptographic wallet software to sign a store-generated message which contains the verification code. The digital signature is delivered to the service provider, which proves the client appeared in-person 480 is the current owner of the wallet and token used during booking. The transfer lock, which was placed at the time of booking guarantees the token is still owned by the client in the same wallet. Signing of the verification code may be performed through a website operated by the service provider by connecting to the client's wallet via its API. The verification request may also be initiated by a push-request sent to the client's phone. The verification data at least includes the in-person verification code and may also include other information to prove mutual agreement, such as the token ID (which identifies the tattoo design, or services/products to be received), agreements or disclosure documents (e.g., liability agreement, terms and conditions, post tattooing care instructions, ID verification). For example, digital packaging of the verification data may be:

Verification data=[in-person verification code; token ID; agreements and disclosures; store ID; date and time]

The verification data may be cryptographically signed using the client's wallet software which may implement a function, for example:

SignMessage(Verification data, private key)

which returns the digital signature. SignMessage may implement a secure cryptographic hash function (e.g. a SHA-2 or SHA-3 function with a sufficient digest length, e.g. 256 or 512 bits) to produce the digital signature.

The verification data and the digital signature may be securely stored for future reference, as proof of in-person presence of the wallet owner. Alternative to the cryptographic verification, the client may provide their full name/ID information at the booking stage (step 320), and a government issued/official ID is checked at the in-person appointment to match the information provided at the booking.

In step 332 the NFT-associated services are executed by the service provider 460 or 112. In the case of tattooing, the tattoo is applied on the client's (480) skin by an automatic tattooing system 470 or 50. In particular, in some embodiment, the automatic tattooing system may directly interact with the blockchain as an authorized operator of the service provider. In some embodiment, the automatic tattooing system may use tamper resistant (hardened) chips (e.g., PUF) to sign and encrypt messages and hold a unique private key for the purpose of interaction with the smart contract 105 and/or the blockchain 440. In some embodiments, the public address of the wallet and the digital signature for the in-person verification data may be transferred to the automatic tattooing system 470, and the digital signature is checked as a pre-requisite to starting the tattoo execution:

isSigned(public wallet address, Verification data, digital signature)

The function call returns logical True if the signature is valid (Verification data is signed by the private key of the wallet address), and False if invalid. The automatic tattooing system 470 or 50 may interact with the blockchain 440 through an interface 121, API, or a secure intermediary server. After validating the digital signature the tattooing system 470 may continue with tattoo execution.

Next, the tattooing system checks whether the services associated with the token are available to be redeemed by querying the function:

Function isConsumed(uint256 tokenId) external view returns(bool)

This function returns True if all services associated with the NFT are already consumed (e.g. all available copies of the tattoo have already been applied), and False if the services can be redeemed. In addition, to support multiple copies to be redeemed from a token, the following generalized function may be implemented:

Function consumableCopies(uint256 tokenId) external view returns(uint256)

This function returns an unsigned integer indicating the number of redeemable services left, where a value of 0 means that all services associated with the NFT are consumed. Execution depends on whether copies are available or not. For example, the tattooing system 470 may require that "isConsumed" returns False or, if applicable, "consumableCopies" returns a number greater than zero, in order to apply a tattoo of the artwork 102 on skin.

Optionally, the automatic tattooing system 470 may also check the validity of the copyright holder's digital signature of the permit certificate. For instance, the copyright license of each copy may be signed by the original copyright owner (e.g., the artist of a tattoo design).

Function CopyPermitSignatures(unit256 token Id, uint256 copyId) external view returns (uint256)

This function returns the digital signature "CopyPermitSignature" of a specific copy of the service (denoted "[tokenId,copyId]") for the copy number "copyId" of the token "tokenId". The copy number "copyId" is retrieved by querying the function ConsumableCopies(tokenId). The automatic tattoo system 470 (or 50 in FIG. 1A) may verify the digital signature by calling the "isSigned" function described earlier:

isSigned(AddressCopyrightOwner,[tokenId, copyId], CopyPermitSignature)

where "AddressCopyrightOwner" is the public address of the copyright owner (e.g. the creator of the tattoo design) saved to the blockchain during NFT creation 305 and may be queried by a function call:

Function CopyrightOwner(uint256 tokenId) external view returns(address)

Any of the above verifications may be set as prerequisites to the operation of the automatic tattooing system 470 in step 332. Machine instructions 111 or other data necessary for execution of the tattoo (e.g., tattoo design 102, decryption keys of the design, etc.) may be acquired through the smart contract 105, conditional on the above verification requirements. The present invention may allow creators, copyright owners or artists 101 using the system to issue NFTs of their work to control the number of copies of their work being used, for example in context of application of tattoo designs on skin, printing of visual artwork, etc.

At step 333, the execution of the tattoo is completed and the applied tattoo is inspected by the service provider and the client. If the outcome of the tattoo is approved, the NFT is marked as consumed via the blockchain operations described in step 340. If the tattoo is not approved, the tattoo execution is adjudicated as described in step 350.

If the tattoo is approved, the operation continues with step 340. The NFT is marked as consumed by calling the function Consume:

Function Consume(uint256 tokenID)

where "tokenID" is the identifier of the tattoo NFT. The function executes if it is called by an authorized address, for example an administrator address, or the address which belongs to the automatic tattooing systems (470 or 50) of the service provider (460 or 112), and is recorded by the smart contract during the booking step 320 of the booking process. For example, the service provider's 460 address "serviceProvider" is set via the "temporaryLock" function call. Upon successful execution, the smart contract sets the "isConsumed" variable for the token to True. In an embodiment that allows multiple-consumptions per token, the Consume function decreases the "ConsumableCopies" variable of the token by the number of consumed copies (one or more). The tattooing system 470 automatically interacts 111 with the smart contract 105 to modify the consumption variable of the NFT 106.

In some embodiments, the following procedure may be implemented to record (i) the proof of tattoo consumption and (ii) the proof of approval by the client (480) of the tattoo outcome. The service provider 112 first collects photographs of the completed tattoo as well as additional information about the tattoo execution data collected by the automatic tattoo system (470), such as skin properties, body position, size of tattoo, skin epidermal texture, executed tattoo puncture parameters and so on. A time-stamp, the store ID, the public address of the token owner, and/or the token ID are then overlaid on the digital image, or combined with the digital photo file in a digital archive file. This combination constitutes the proof of consumption:

ProofConsumption=[Photo of the applied tattoo, tattoo execution data, date-time, store ID, token owner address, token ID]

A hash of the proof of consumption is then calculated, for example using the SHA-256 algorithm:

hash(ProofConsumption)→hashProofConsumption

Optionally, the proof of consumption may be kept in private records of the service provider, uploaded to an online public storage, or uploaded to a distributed file storage system, e.g., IPFS, which uses the hash as the content identifier/indexer for public verification. Using the hash as the content identifier guarantees that the evidence of consumption cannot be tampered with later on. The service provider may request that the customer cryptographically signs the proof of consumption, which could be done on a mobile device initiated by a push-notification:

sign(hashProofConsumption,OwnerKey)→OwnerSignature

The combination of [hashProofConsumption,OwnerSignature] constitute the proof of client's approval of the tattoo outcome. The proof of consumption and/or proof of client approval may be retained off-chain for records, or may be submitted to the NFT smart contract as an argument of the Consume function, in order to be recorded on the blockchain:

Function Consume(uint256 tokenId,uint256 hashProofConsumption)

Function Consume(uint256 tokenId,uint256 hashProofConsumption,uint256 OwnerSignature)

These function sets the proof of consumption variable as ProofConsumed[tokenId]=hashProofConsumption, which may be later queried publicly by a function call, e.g. ProofConsumed(uint 256 tokenId) external view returns (uint256). An optional argument "OwnerSignature" may be implemented, to set the external query variable as ProofApproval[tokenId]=OwnerSignature, and therefore keep a public record of the proof of client's approval.

In addition to the proof of consumption and/or the proof of approval, the owner's name, preferred name or nickname may be recorded on the blockchain, which may be queried publicly as a record of the recipient of the tattoo.

Optionally, a blockchain operated escrow smart contract may be implemented to retain the service/execution fees and release them to the service provider upon a successful tattoo application and/or approval of the client, as shown in step 341.

In embodiments which implement an escrow, the client may place the service fees on escrow by funding the NFT smart contract with cryptocurrency (msg.value). This escrow payment may be done (i) at the time of initial token purchase 310 (token has pre-paid service fees), (ii) at the time of booking 320, or (iii) at the store by the NFT holder before tattoo execution begins. Presence of a service fee pre-payment for tokens may be queried through the smart contract:

Function AmountSeryiceFeePaid(uint256 tokenID) external view returns (uint256)

If the service fees are pre-paid, the token may have a higher inherent value on the secondary market. The smart contract function for placing service fees on escrow may be:

Function EscrowServiceFees(tokenId) external payable

The function may require the caller (msg.sender) to be the current owner of the token, and may also require the payment sent is above a minimum required service fee defined by the variable MinimumServiceFee[tokenId]. Upon successful execution, the function increases the variable AmountServiceFeePaid[tokenId] by the received payment amount. The escrowed funds may be claimed by a service provider and upon submission of mutually-agreed upon proof of consumption (steps 340, 341), or may be refunded to the token owner if the tattoo execution fails (see step 362).

After a successful application of the tattoo, in some embodiments, the proof of client approval [hashProofConsumption, OwnerSignature] may be submitted to the escrow smart contract, and the contract may release the funds to the service provider's address if the token owner's digital signature is valid (step 341).

Function ReleaseEscrowedServiceFees(tokenId, hashProofConsumption, OwnerSignature) external payable The function requires the caller is an administrative address or the service provider's 460 address ("serviceProvider" set earlier with the temporaryLock function call). The function verifies the client's digital signature on the proof of consumption by calling the cryptographic function:

isSigned(hashProofConsumption, ownerOf(tokenID), OwnerSignature)

The function then proceeds to release the escrowed service fees AmountServiceFeePaid[tokenId] to the address of the "serviceProvider" as a blockchain payment, and sets AmountServiceFeePaid[tokenId] to zero.

In another embodiment, the store may submit a proof of consumption to claim the service fees held in escrow:

Function ReleaseEscrowedServiceFees(tokenId,hashProofConsumption) external payable In one embodiment, "ReleaseEscrowedServiceFees" may be called from the client's address. In this case, the call is interpreted as the proof of approval by client, and the escrowed funds are released to the service provider's wallet. To facilitate the approval process, a push-request sent to the client's mobile device to initiate this function call upon confirmation.

The NFT may be allowed or dis-allowed to circulate after the services are redeemed. If allowed, the temporary trading lock placed in step 323 is lifted in step 345, to allow trading of the service-consumed NFT:

function temporaryUnlock(uint256 tokenId);

This function initiates unlocking of transfer of an NFT. The function throws if the NFT is already unlocked. The function throws if the NFT is permanently locked. The function throws unless msg.sender (caller of the function) is the minting party of the NFT or the approved operator of the minting party of the NFT listed as "serviceProvider" in the temporary lock event. The function throw if "_owner" is not the owner of the NFT. The parameter _owner is the current owner of the NFT, the parameter "serviceProvider" is the service provider for the application of the tattoo and the parameter "tokenId" is the identifier of the NFT.

event TemporaryUnlock(uint256 tokenId);

This event is emitted when an NFT temporary lock is lifted.

Unlocking transfers enables transfers of the token between users on the market 450. However, note that due to consumption of the services (reflected by the "isConsumed" variable set to True, or by lower values of the variable "ConsumableCopies") the token's inherent value and its traded price on the secondary market 450 may be reduced.

If the token is not allowed to circulate after service consumption, a permanent lock may be applied in step 346 by calling the function:

function permanentLock(uint256 tokenId);

This event may be emitted when a token is permanently locked for transfers:

event PermanentLock(uint256 tokenId);

The execution of the tattoo or other associated-services may be considered failed, in step 360. In step 361 the client and the store may agree on scheduling a future appointment to attempt another execution. In this case, the temporary lock placed at step 323 remains on the token, and any pre-paid service fees may remain on the escrow account of the smart contract. If the client prefers not to book another appointment at the store, the store releases the temporary lock in step 363 using the function temporaryUnlock( ) presented above.

The prepaid funds on escrow are released to the client in step 362. Step 362 may not be allowed if the service fees were pre-paid during the initial purchase (310) by another user. In some embodiments, the refundable fees are refunded automatically to the client (ownerOf[tokenId]) in the temporaryUnlock function call before lifting the transfer lock. In other embodiments, the refund of escrow funds may be initiated by the following smart contract function call:

RefundEscrowedServiceFees(tokenID)

If the caller of the function is the token owner 480, the function may require that the temporary lock has been lifted (isTransferLocked[tokenId] is False) which indicates a failed or relinquished tattoo execution (step 360). Alternatively, the caller may be the service provider 112, in which case the funds are refunded to the client's 480 address.

Optionally, the tattoo may be marked not consumed in step 364. This optional step may occur if the tattoo was denoted consumed at step 323. Indeed, in order to limit the number of calls to the smart contract and its related gas or transaction fees, it may be preferable to lock and consume the contract at the booking step 323. In this way, if the tattoo is approved in step 333, the smart contract does not need to be accessed after execution. Note that in the case where the tattoo is redeemed in step 323, step 340 to 346 may be omitted as well. At step 365, the client may be offered other compensation, services, or reimbursement as a compensation for the failed execution of the services. The process ends in step 370.

At least some embodiments of the invention can include the potential transfer of a locked NFT. The wallet owner may want to move the locked NFT to another wallet without involving a payable transaction, for example when an NFT owner may want to transfer the NFT between two wallets they own. For example, to transfer the locked NFT the system can employ the approval function (e.g., an approval function defined in the ERC 721 standard or another standard) and a modification of, for example, the safeTransferFrom and transferFrom functions. The transfer functions may be modified to operate even with the transfers locked, such as if (1) the message sender is the NFT administrator or its operators and (2) the NFT administrator or its operators have been defined as approved operator of the NFT by the NFT owner (e.g., by calling the approval function of the ERC721 standard). In this way, the NFT owner is still blocked from the transfer of a locked NFT but may rely on the NFT administrator and its operators to act as proxies for the transfer. This allows the NFT administrator or its operators to evaluate if the NFT transfer is within the expected use (e.g., as specified in the smart contract) of transfers of locked NFTs, such as between wallets owned by the same owner, and reject transfers which involve a monetary or token exchange. Further, in some embodiments, the NFT may be transferred to a wallet address defined by the function setBeneficiary.

In some embodiments, the NFT owner and its operators may operate a modified transfer function for a locked NFT if they received a signed message as an authorization from the NFT administrator or its operators. In some embodiments, the NFT owner may define a beneficiary, such as a wallet that may receive the NFT using a function in the smart contract such as:

setBeneficiary(address_beneficiary, uint256_tokenID)

This function may be used to define the wallet address of a beneficiary ("_beneficiary") for a specific token, identified by the argument "_tokenID". This function may be operated by the NFT owner or its operators. The defined address of the beneficiary may be used by the NFT owner, administrator, or their operators, to initiate a transfer of the NFT.

An example method is the transfer of an NFT from one wallet to another, where the NFT owner owns both wallets. This may be verified by the NFT operator using an authentication method where a message may be signed by both wallet keys to verify that they are indeed operated by the same owner. Another example method is for the recovery of an NFT in the case of lost wallet credentials. It is possible that a wallet owner loses possession of their private key and therefore be incapable of accessing their NFT, locked or not. The NFT administrator may use the visual identification method described in this disclosure or a government-issued ID information to transfer the locked NFT to a new wallet on behalf of the tattoo owner.

Another example method is the definition of a beneficiary following the passing of the NFT owner which has an associated tattoo. It can be common for family members or friends to tattoo copies of their loved one's tattoos on themselves after their passing. By enabling a beneficiary during their lifetime, a tattoo owner may create the possibility of the transfer of a tattoo to another person after passing. The NFT administrator may verify death certificates and compare them to ID of the tattoo owner to establish the transfer of the associated NFT. In some embodiments, the consumption flag of a tattoo service associated with the NFT may be switched from consumed to non-consumed to allow the beneficiary to receive the tattoo. The NFT may remain locked in the process.

One embodiment of this invention is the use of the NFTs after the execution of the tattoo as certificates of both authenticity and ownership using an automated identification method by an observer using a certification application that operate image acquisition, identification and verification. Such an application may operate on machines integrated to the tattoo system 50 of FIG. 1A. The tattoo system 50 may operate the certification application to capture images of finished tattoos that may be used as proof of completion of a tattoo. In particular, this may be operated by the controller 58 of FIGS. 1A-B. The application may also be used for high resolution imaging of tattoos to denote the state of the tattoo after aging. Another application is to capture fine texture of the skin for biometric application purposes. Such a certification application may be operated on a personal computing and imaging device such as a personal computer equipped with camera or other portable computing devices such as tablets and smartphones, smartwatches and the like.

Authenticity may be established visually by the presence of a trademark integrated in the design. This may be identified by people by observing the design directly or through the intermediary of an imaging device. The imaging device operated by the certification application may use a machine vision routine to identify the trademark and compare it to the brand trademark to verify correspondence. This can be done using methods in the certification application such as affine- and scale-invariant feature transform, maximally stable extremal regions, local invariant features, affine-Forapro, affine-Ciratefi, etc.

The certification application may contain an imaging subsystem for the collection of images or series of images that facilitate imaging of the tattoo for the purpose of identification. Such a system may overlap control on a visualization screen (e.g., 59 of FIG. 1C) for the observer to select appropriate viewing distances, angle of viewing, focusing, lighting condition and the likes. Such an application may enhance the quality of picture by using image composite through hyper resolution, AI augmentation or the like. The certification application may access the camera interface to modify image acquisition settings such as gain, exposure, resolution, framerate, white balance and the likes, in order to enhance imaging of tattoos on skin. The image quality subroutine of the certification application may be operated in real time such that the application may provide real time feedback to the operator when appropriate imaging conditions are met. For example, if the outline of a tattoo is detected clearly, it may appear outlined on the imaging screen of the device running the application. Focus enhancement and saturation markings may be further added to the image to indicate proper focus and dynamic range in order to improve image gathering. In some embodiment, the certification application may continuously acquire images and proceed with real time image approval, rejection or composition to capture the imaging data and indicate to the observer when sufficient images of quality have been gathered. The application may invite the observer to continuously change their point of view to gather better or complementary images during this continuous process. The certification application may only operate if minimum image quality is possible with the device it is installed upon. For example, the application may require image resolution higher than HD. In some embodiments, image resolution requirement may be different based on the required identification routine. For example, imaging a QR code may require only 1 pixel per 500 μm of imaged skin, while texture identification may require 1 pixel per 5 μm of imaged skin. Collected images may be analyzed after the image acquisition routine.

In some embodiment, the certification application may be operated on the digital market interface. Note that some image correction may be necessary to interpret images of tattoos on skin. Parallax, body part gross geometry, skin deformation and other physical transformations may result in a deformed image of the tattoo area. A preprocessing step may be taken by the certification application to compensate for linear and non-linear transformations resulting from these effects and an inverse transformation of the image may first be found to prepare the image for fit. In some embodiment, this inverse transformation may be applied in an iterative manner with progressive machine vision fit to gradually improve the image match error. The total inverse transformation may then be analyzed to verify that the associated transformation is consistent with physically possible transformation due to parallax, body part geometry, skin deformation and so on. Additional images from different viewpoints may be requested to improve image interpretation. Note that all images in this section of the document may also be continuous streams of images, such as videos.

The uniqueness and ownership of a tattoo with a trademark may be further established by the presence of human or machine readable alphanumerical or symbolic markings that would let a person or a machine read it. In some embodiment, no trademark is used and the marking for uniqueness is used to establish authenticity For example, the hash of the tattoo design listed in the NFT metadata may be part of these markings facilitating NFT retrieval. In another example, the markings may list the collection name and NFT number which may be searchable on an NFT marketplace. In yet another example, a QR code may be present that may be read by a personal imaging device, and contains a hyperlink of the NFT. Other barcode type markings such as DataMatrix and Aztec may also be used. The observer may then manually compare the design in the NFT with the tattoo. Further, these additional markings may be identified by machine vision methods similar to the one used to identify the trademark. In these embodiments, if both or either or one of the trademarks or the unique markings do not correspond to an authentic trademark or unique NFT, the tattoo is deemed unknown.

However, this certification is not safe from forgery because the tattoo may be denoted as corresponding to the one in the NFT chain, but no verification is performed to establish that it is not a high-quality forgery. Furthermore, markings may not be wanted since these affect the aesthetic of the tattoo. One embodiment of the invention proposes to enhance this with peer-to-peer identification and verification of wallet ownership. This may be done by the wallet owner signing an authentication challenge to verify that the tattoo owner is the NFT owner. Further, and in the case of NFT redeemed as presented in this document, the proof of execution document (step 340 in FIG. 3) can further contain information pertinent to tattoo placement, ink color, skin information and tattoo size that can provide additional proof of authenticity and uniqueness for the tattoo.

The method for identifying trademarks and other markings operated by the certification application may be operated on a personal computing and imaging device may be operated automatically through a mobile application. This mobile application may be installed on the observer's device and tattoo owner device for tattoo identification, authentication and validation using routines of the NFT smart contract or other routines. A more detailed explanation of the application is given below. In some embodiments, a trademark or additional markings beside the tattoo are not integrated to the design.

In some embodiments of tattoos robotically applied, it is possible to prescribe the placement of the needle punctures that deposit ink in the skin. One or more punctures executed at the same location in the skin can form identifiable dots. Many dots may be used to form tattoos by drawing lines and fill areas with various gradients by varying dot to dot distance (where further apart dots may appear to form an area of lighter shade compared to dot closer together) and dot ink amount (either by placing more or less punctures per dot to increase or decrease ink deposition or by increasing or decreasing depth of the needle in the skin, to increase or decrease ink deposition). Because line and area gradients can be formed by multiple parameter choices such as placement of punctures, number of punctures per dot and puncture depth, it is possible to encode information by locally varying these parameters within a design without significantly changing the design aesthetic from the perspective of a human at a usual viewing distance. However, personal imaging devices can achieve imaging resolution that can detect the varying parameters used within a tattoo design at the time of application. It is then possible to perform minute variation in the design that encode for unique identifier information that can be detected through a personal computing and imaging device method. For privacy reasons, this encoded unique identifier information may relate to a unique tattoo execution event (332 or 340) or the unique NFT token, rather than directly to the identity of the client.

Here, we describe this method, which may run on the certification application. First, the imaging subroutine of the certification application may provide machine vision data such as qualified images and their composites. Then, a global identification of the tattoo is performed. A tattoo may be recognized by its design, for example, a tattoo of a dolphin may be identified separately from a tattoo of a banana (or a slightly different dolphin design) through pattern recognition or another of the image recognition methods cited above. The design may be compared with a database of tattoos performed on skin by reading a database of redeemed NFTs. This first global identification let us identify which design was used for the tattoo. A local analysis may then take place. New images may be acquired by the application for higher definition imaging based on pattern recognition quality. Because multiple tattoos of the same design may be tattooed, and because forgery may match the global design, local pattern recognition may be necessary. In this step, variations in the design may be identified. These variations are used to identify a specific tattoo in a group of tattoos that have the same design or to further the difficulty of forgery for a specific design. In some embodiments, the tattoos can include machine-readable identification features (e.g., machine-generated dots or bar codes capable of being identified by an optical tattoo analyzer, such as an analyzer with a high-resolution scanner or digital camera. The machine-identifiable features incorporated into the tattoo generally not visible to the naked eye from normal viewing distances (e.g., 2 feet, 3 feet, 4 feet, etc.), such as small round dots incorporated into the tattoo.

Figure 5:
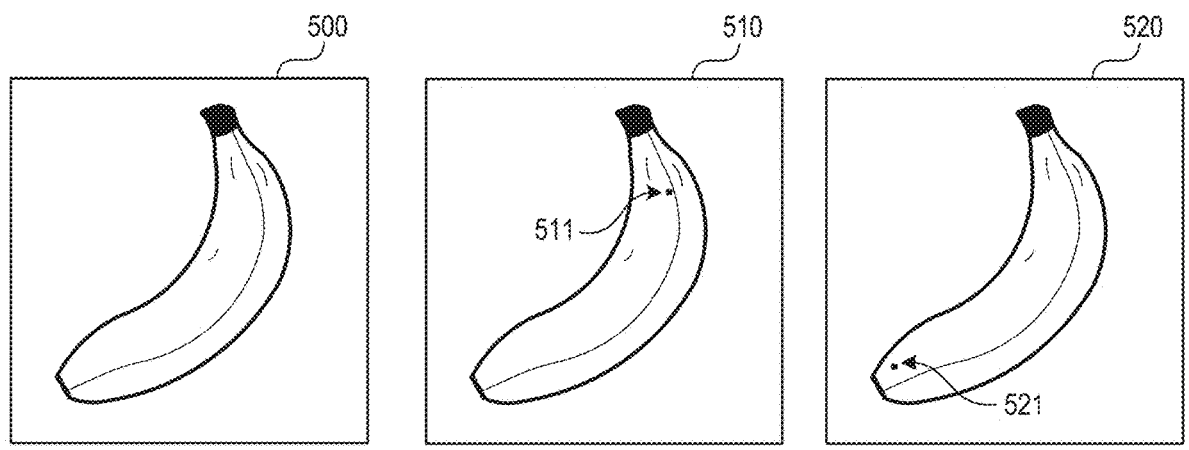
FIG. 5 illustrates an example of a tattoo image, in accordance with one or more embodiments of the present technology.

FIG. 5 shows a banana example. Both banana 510 and 520 tattoo look globally identical to the original design 500, however, a dot 511 is present on banana 510 that is not present on banana 520, and conversely, a dot 521 on banana 520 is not present on banana 510. It is then possible to distinguish between the bananas 510 and 520. The design associated with both NFT associated with tattoo 510 and 520 may be the original design 500, which doesn't contain the uniquely identifiable features of tattoo 510 and 520. As a result, it becomes exceedingly difficult to make a forgery as access to a high-quality design of the actually tattooed art is difficult. Actual dot parameters used by the robotic tattoo machine during the application of 510 and 520 may be encrypted and the routine for identification of tattoos may be run in a secure cloud application thus the variations of each tattoo may be undiscernible without having access to all the tattooed versions of the banana 500. The dots 511 and 521 can be identifiable markings used to identify the tattoo and can be invisible or barely visible to the naked eye. A high definition and quality camera can identify the dots in the tattoo image to verify the tattoo as the tattoo of the NFT. For example, cameras with imaging resolution that are better than 200 µm per pixel on the skin may be required. Note that the example of FIG. 5 involves a couple of dots added to 510 not present in 520 and vice versa. In practice, many variations may be integrated to a tattoo involving both addition and deletion of dots, position perturbation of dots, variation in number and depth of punctures and so on. This may create a redundant identification pattern where many variations may need to be observed to identify the design and its related NFT. Next, NFT execution proof is read and compared to the tattoo image. Such execution proof contains positioning information, size and orientation of tattoo, type of ink used and skin features such as shade, moles, crease etc. Comparing this execution information with the pictures further establishes the authenticity of the tattoo.

While this method may not validate that the tattoo owner is the NFT owner, the hurdle of forgery is significantly higher. A convincing forgery would need to have access to high-quality images of the original tattoo design and the ability to replicate its minute variations. Such a feat would be possible with a robotic tattoo machine with as good or better resolution as the original. Note that tattoo aging further amplifies the difficulty as a new tattoo doesn't look exactly the same as an old tattoo.

Further, and since the NFT execution data contains owner specific information about body position, visible skin features such as moles and skin shade, tattoo size and orientation, any forgery is significantly at risk to be identified as such if tattooed on people with significantly different features. The method therefore may be used to check or prove the authenticity of a tattoo on skin. Furthermore, by embedding and verifying the license in the NFT (i.e., with function "copyPermit") as described in steps 305 and 332 of FIG. 3, this method is also used to prove that the tattoo was performed with license from its creator or copyright owner 101.

One embodiment of the invention proposed prior is to enhance this identification/authentication method with a peer-to-peer verification of wallet ownership. This may be done by the wallet owner signing an authentication challenge to verify that the tattoo owner is the NFT owner. This may be done using a mobile app running the following method. Once the NFT related to the tattoo design is identified, the identity of the wallet owner containing the NFT may be queried using the query approach listed in the ERC 271 standard (i.e., the function "ownerOf") or by a query to a third-party database, custom smart contract function or service listing such ownership. A request for a digital signature may then be sent to the wallet owner. This may be done with a variety of processes such as by sending a an off-chain push notification to the mobile app, querying a wallet API, requesting the operation of an event generation function of the NFT smart contract executable by the wallet owner and so on. In general, a specific unique message, involving exchanging a code from the observer to the tattoo owner, shall be sent by the observer to the tattoo owner. The tattoo owner may then sign the message cryptographically. The observer can then verify, for example through a mobile app or other interface, that the cryptographic signature corresponds to the public key of the NFT owner or that an NFT event was triggered by the wallet owner including part of the observer's message or code.

Note that this process requires that a message must be first sent to the tattoo owner and that the tattoo/NFT owner must then proceed cryptographically signing the message. This clearly requires intervention from the tattoo/NFT owner, such as exchanging an in-person message, for example a four digits code. This process can be simplified by peer-to-peer communication between the tattoo owner's and observer's devices. If the tattoo owner possesses a copy of the mobile application, a direct device to device wireless connection, such as Bluetooth, Wi-Fi or other wireless protocol may be used to send the message to be signed from the observer to the tattoo owner. The signing may then be directly operated through the same channel, through the internet or through an alternate channel. The action of sending and signing a message may be operated by the mobile application directly if recognized as an operator of the observer and wallet owner without involving an action from the owner or the observer at the time of the verification request. The observer may then verify authenticity of the tattoo without the owner's intervention. In some embodiment, the authorization of the tattoo owner may be required to proceed with the authentication of the design to preserve the tattoo owner privacy. This authorization may precede tattoo identification if the tattoo owner opts out of this service, in which case, the method for identification of the NFT associated with the tattoo may be deactivated and no NFT information or identification is shared with the observer. In other embodiments, the identification may identify whether the tattoo is authentic and associated with an NFT but without revealing either the NFT address or the NFT owner.

In some embodiments, a global identification is performed and multiple NFTs may be associated with this global identification. In this case, peer-to-peer identification may be attempted before peer-to-peer validation. This step may involve a request for wallet ID of the tattoo owner. An NFT associated with the global tattoo design identification may then be verified as being owned by the offered wallet ID prior to message signing.

In some embodiment of the invention, authenticity may be obtained by professional equipment using biometric information. For example, NFT tattoo execution data may also relate to unique fiducial features such as skin epidermis folds. These skin epidermis folds are as unique as fingerprints and their analysis can uniquely identify the skin onto which the tattoo is performed. Current personal imaging devices that can resolve skin folds are not common, and imaging with professional equipment may be necessary in this step. This type of analysis is therefore an optional part of comparing the tattoo execution data to the images of the tattoo.

Figure 6A:
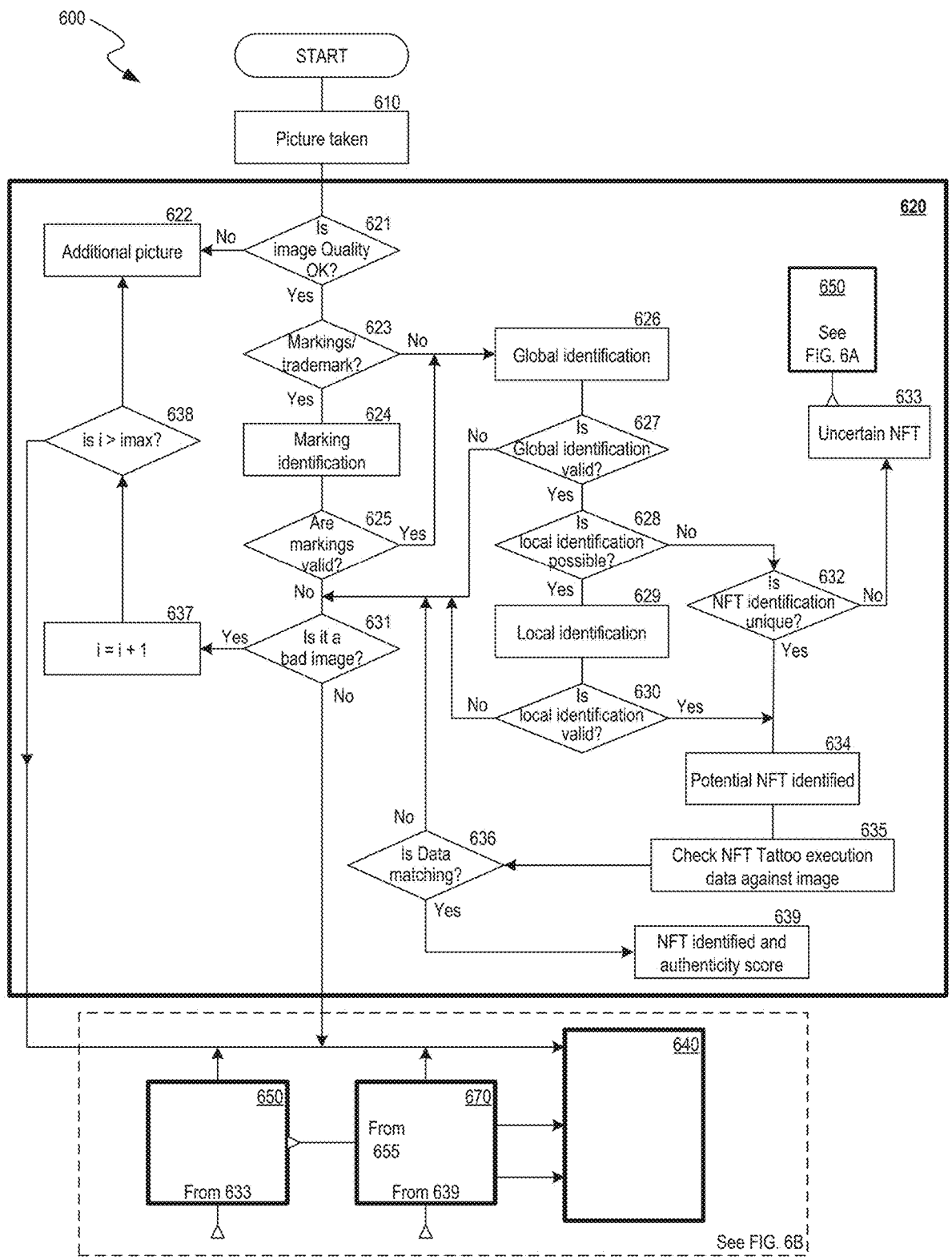
FIGS. 6A-6B are flow diagrams illustrating processes of visual identification, peer to peer identification and peer to peer validation which lead to the outcome of authentication and unique identification, in accordance with one or more embodiments of the present technology.

FIG. 6A illustrates a process 600 of visual identification, peer to peer identification and peer to peer validation which lead to the outcome of authentication and unique identification. Such a process is operated by the certification application. This set of methods may be operated on the tattoo system 50 of FIG. 1A, in particular a controller 58, or personal computing and imaging devices with access to peer-to-peer communication and server or internet access. First, as in step 610, the observer may operate the certification application presented above. The certification application permits the capture and identification of images. The captured images are first checked for quality in step 621 and a request for new captures 622 may be initiated if the image quality is not good enough, such as blurry, too much parallax, not resolved enough and so on. For example, the images may have a threshold number of pixels per area, color rendering, or signal to noise ratio to be determined acceptable. Such as a maximum pixel size in the range of 50 μm to 1 mm when compared to the scale of the imaged body part. For instance, marking identification and global image identification may only require 500 μm per pixel resolution, while local identification may require 200 μm per pixel and better. In some embodiments, the new picture 622 can be generated based on the quality check of step 621. For example, the system can determine camera settings (e.g., resolution settings, focus settings, etc.) of imaging devices to obtain additional pictures with suitable data. For example, the system can determine settings for the imaging device 56 of FIG. 1A, camera input device 72 of FIG. 1B, or other imaging devices disclosed herein. This allows the system to analyze tattoos to obtain pictures with sufficient data for authentication. Once an image or set of images passes the quality test of step 621, the images are analyzed for markings beside the tattoo such as trademarks and machine/human readable markings. If markings are present, the markings are analyzed in step 624. As explained above, the markings may be symbolic or alphanumerical markings besides the tattoo. For example, the markings may list the collection name and NFT number which may be searchable on an NFT marketplace. In yet another example, a QR code may be present that may be read by a personal imaging device, and contains a hyperlink of the NFT. Other barcode type markings such as DataMatrix and Aztec may also be used. If the markings are not recognized, the images are analyzed once again to verify if the markings are not recognized due to bad pictures in step 631. If it is a case of bad images, an iterative loop is initiated in step 637 iteration index and 638 iteration check to initiate a new request for pictures in step 622 and restart the process from step 621. If the number of iterations exceeds a number imax in step 638, the tattoo is deemed unknown in step 641. If the quality of the images is appropriate at step 631, it means the markings were unknown and the tattoo is deemed unknown in step 641.

If there are no identifiable markings in step 623, or if the markings are deemed valid in step 625, the process continues in step 626 for a global identification of the design. In step 626 the design is analyzed as described in earlier paragraph to find a fit with known tattoo designs. If the global identification finds no valid fit in step 627, then step 631 evaluates if it is caused by a bad image and subsequent steps to 631 are performed as in the previous description. If the fit is found valid in step 627, then the process proceeds to step 628 to check if local image analysis is possible for that tattoo design. If it is not a used feature, for example, for tattoos that do not have local variations added in for enhanced identification, it proceeds to step 632. If there is one NFT associated with the design identified in steps 626-627 or if the markings uniquely identify a single NFT, then 632 proceeds to step 634, as a potential unique NFT was identified for the tattoo which was pictured in step 610. If there is more than one NFT associated with the tattoo design or if the markings do not indicate which NFT is associated with the tattoo images, then the process proceeds from step 632 to step 633.

In step 633, the design of the tattoo and or markings have been identified but no unique match between a specific NFT and the tattoo image was found. Back in step 628, if local image analysis is possible for this tattoo image, local analysis is attempted in step 629. The local analysis identifies minute variation in the visible puncture parameters that may uniquely identify the tattoo authenticity and uniqueness. The confidence level in the identification and matching of the local features is evaluated in step 630. If no acceptable match (above a minimum confidence level) is found within the known set of encoded variations, then the images are analyzed once again for quality in step 631 and subsequent step. If a match is found, then it proceeds to step 634 as a potential unique NFT was identified. After step 634, the process advances to step 635 to check if the NFT tattoo execution data matches with the images of the tattoo. These tattoo execution data (see step 340 in FIG. 3) reflect information such as the type of ink, position on the body, visible skin features such as moles and skin shade, tattoo size and orientation and so on. The level of match between the NFT execution data and the picture(s) 610/622 of the tattoo is evaluated in step 636. If the NFT data does not sufficiently match with the pictures, the process advances to step 631 and its subsequent steps. If the NFT data matches the pictures the process advances to step 639. In step 639, a unique NFT was identified. Additionally, a confidence index (authenticity score) may be calculated in step 639 as a measure of the confidence in the determined authenticity. A confidence index above a threshold can indicate authenticity. A matching of images which relies on the global image analysis 626 results in a lower confidence index than an identification obtained through matching the local features/variations and with markings. This is because the hurdle of replicating the local features/variations for a forgery is significantly higher. The confidence index is also adjusted by the level of error in matching of the local features, which may be affected by the image quality. A match with low error will result in a higher confidence index than a match with high error. Finally, the degree of matching with the tattoo execution data related to the NFT may improve or degrade the confidence index. The confidence index may be displayed in step 642 and 643 at the end of the process, once compounded with the result of block 670 of peer-to-peer validation. In some embodiments, the process doesn't attempt peer to peer communication (i.e., identification of step 650 and validation of step 670 of FIG. 6B) and the output is instead the one of step 639, 633 and 641.

In some embodiments, a tattooing machine may use the certification application to determine a confidence level or index. A user can select a confidence level (e.g., greater than 90%, 95%, 98%, or 99% likelihood of match) for proceeding. The tattooing machine can identify through the certification application, via a cryptographic signature, the subject as an owner of artwork to be applied. This certification application may be used by a tattoo system 50 for the subsequent identification of wallet users for the purpose of performing more tattoos. For example, the controller 69 or 58 of FIG. 1A can identify the subject matching the cryptographic signature at block 670. In response to identifying the subject as the owner, the tattooing machine can robotically apply a tattoo of the artwork to the subject and capture authentication images (e.g., using the optical tattoo analyzer 56 of FIG. 1A) subsequently used at block 620. The tattooing machine can then authenticate the applied tattoo based on the artwork using the captured one or more authentication images.

Figure 6B:
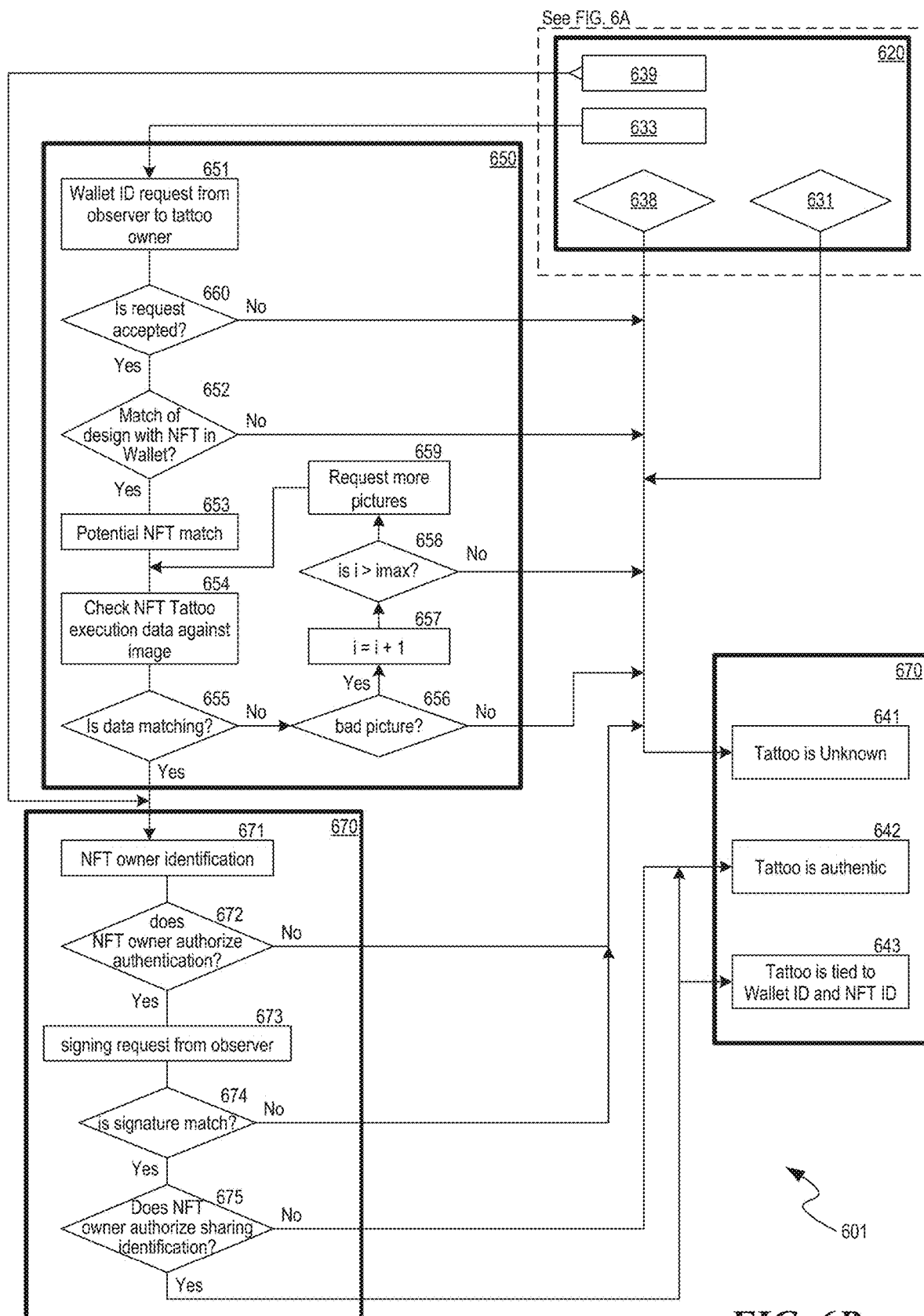

FIG. 6B illustrates a process 601 of visual identification, peer to peer identification and peer to peer validation which lead to the outcome of authentication and unique identification. Peer to Peer Identification block 650 is performed if the process of block 620, image identification, ended at step 633, when the design of the tattoo was identified but no match between a specific NFT and the tattoo was yet found through image processing. Peer to Peer identification is done by establishing a wireless connection between the device of the observer and tattoo owner such that a request for wallet ID is sent in step 651. In step 660, if wallet ID request was denied, such as in the case where the tattoo owner opt out of sharing information, the system proceeds to output step 641. If the request is complied with, the process advances to step 652. In step 652, it is verified that one or more NFT(s) that match the identified tattoo design have been tattooed on the owner of the provided wallet ID. If it is not the case, the system proceeds to output step 641. If it is the case, the process advances to step 653, where a potential NFT match or matches are found. Step 654 checks if the NFT tattoo execution data of one of the NFT matches fit with the images of the tattoo. The match can be based on a predicted resolution of the tattoo. The predicted resolution can be based on the subject's skin characteristics, resolution of robotically applied tattoos, skill of tattoo artist (e.g., skill rating of tattoo artist) for manually applied tattoos, type of tattoo (e.g., micro tattoo, realism tattoos, blackwork tattoos, etc.), etc. For example, the predicted resolution of the tattoo can be correlated to the dots per area of a robotically applied tattoo. The fit between the NFT execution data of each NFT match and the image of the tattoo is evaluated in step 655. If the NFT data doesn't match with the pictures of any of the NFT matches of redeemed NFT of the wallet owner, the process advances to step 656 where picture quality is evaluated. The process of step 656, 657, 658 and 659 reflects steps 631, 637, 638 and 622 respectively. Step 659, where a new picture is requested, advances the process back to step 654. If the iteration check of step 658 exceeds a number of iterations imax then the tattoo is deemed unknown in step 641.

Back in step 655, if the NFT execution data of one of the NFT matches the image in the tattoo, the process advances from block 650, peer to peer identification, to block 670, peer to peer validation, at step 671.

Step 671 is the first step of block 670 and it follows either step 655 or step 639. In step 671, the owner of the NFT associated with the tattoo is identified. This may be done by using a function on the NFT smart contract (such as ownerOf). The process advances to step 672 to check if the NFT owner authorizes authentication. This may be done by a request sent to the owner, by checking a state in the NFT smart contract or NFT events, or by checking a database. Such flag or state can be updated by the NFT owner using a smart contract function or opting in or out in a client database or an app query, at the time of the check by the process or at a previous time. If the NFT owner decides not to allow authentication of their tattoo in step 672, the process advances to step 641, unknown tattoo. If the NFT owner allows authentication, the process proceeds to step 673, signing request. In that step a message is sent in a direct peer to peer fashion from the observer's device to the tattoo owner's device. The message may then be signed cryptographically (e.g., using asymmetric cryptography) to ascertain that the tattoo owner is also the NFT owner. For example, a Bluetooth connection or other wireless connection may be established between the devices of the observer and the tattoo owner, both operating the certification application. The certification application of the observer may send a message to the application of the tattoo owner. The certification application of the tattoo owner may sign the message by hashing the message and encrypting it with the wallet owner private key (e.g., by raising the hash to the power of the private key). The signed message may then be sent back to the observer's application and the encrypted hash may be decrypted with the wallet owner public key (e.g., by raising the signature to the power of the public key) to verify that the resulting hash is the hash of the original message. Typically, the signing is performed with protocols such as SHA-2 and SHA-3. This may also be done through the intermediary of a smart contract function on the blockchain that changes a state including the message, then queried by the observer. The process advances to step 674 to check if the signature matches. If the tattoo owner is not the NFT owner, or if no signature or author authentication hurdle was met or attempted by the tattoo owner, step 674 proceeds to step 641, unknown tattoo. Else, if the signature challenge was met the process advances to step 675, authorization of sharing identification. The NFT owner may opt out of having his wallet ID and NFT ID shared with the observer in step 675. If this is the case, the process advances to output 642, where the tattoo is revealed to the observer to be authentic. If the NFT owner authorizes sharing the NFT ID and Wallet ID, both step 642 and 643 follow step 675, and both the tattoo authenticity, its associated NFT ID and wallet ID are revealed to the observer.

Steps 641, 642 and 643 are part of the output block 640. Step 641 may display a message to the observer that the tattoo is unknown or that the tattoo owner opted out of authentication. Step 642 by itself displays a message to the observer that the tattoo is authentic but that the tattoo owner opted out of NFT or wallet identification. Note that wallet and NFT identification are not separable in a public chain because knowing the NFT ID readily avails the wallet ID. This may be different on a private chain or a database. If both step 642 and 643 are reached, the tattoo is revealed to be authentic and its NFT and wallet ID are displayed. Moreover, information about that specific tattoo and any unique NFT associated content may be revealed to the observer. Note that in some embodiments, the observer and the tattoo owner are the same individual. Note that one tattoo owner may own more than one wallet.

In some embodiment of the invention, the identification and authentication method presented above may also be used to identify the wallet ID of the observer. That way, authorization for access to tattoo identification could be observer specific, where the NFT owner may restrict authorization to specific other wallet IDs or blacklist some wallet IDs.

In some embodiments of the invention, temporary tattoos may be used instead of permanent ones.

Tattoos may change and degrade over time. First rapidly in the first 60 days of healing then more slowly due to sun exposure, mechanical and biological factors and so on. Further, tattoos may be damaged by subsequent trauma to the skin such as by a cut or a burn.

If nothing is done in the visual identification method (block 620 of FIG. 6A) to compensate for this, the match between the tattoo image and the corresponding tattoo design will gradually degrade with the risk of being unrecognizable.

Some embodiments of the invention relate to the update of the matching database to account for the evolution of the tattoo. The first way to reduce the impact of this effect is to produce redundant features in the original design that can be uniquely identified by imaging and that are less prone to degrade. One process to keep track of degradation relates to continuous data accretion for accounting for tattoo change. Another process relates to tattoo aging simulation. Another process relates to high-definition scans to refresh the database. Yet another process relates to tattoo touchup to improve data match. These processes may operate together to continuously account for changes in the tattoo and guarantee visual identification In some embodiments, tattoo designs are optimized such that degradation over time minimally impacts their fit through imaging. One strategy is to improve redundancy such that identification may be reached by observing a subset of the tattoo. For example, more than one variation may exist between two tattoos that look alike, such that if some of these variations are unidentifiable due to tattoo degradation, a unique identification is still possible. Another strategy is to create identification features that may resist degradation. For instance, one big dot far from other features has a better chance of being identified than a small dot close to other features. This is because the main effect of tattoo aging is the diffusion of ink which may make features close together fuse and not be distinguishable. There is a limit to this optimization as the more degradation resistant the tattoo is for identification purposes, the more it deviates from the original tattoo design to the point of being a departure from the original art. Some tattoos may be specifically designed to be long lasting and clear for the purpose of machine vision identification, notably if their utility is through identification rather than for aesthetic purposes.

In some embodiments, continuous data accretion is used to account for the changes in the tattoo. The key concept of this process is to use prior successful identification of the tattoo to keep track of tattoo evolution. Say an observer has collected images and successfully identified a specific tattoo with a process such as the one described in relation to FIGS. 6A and 6B. The images collected by the observer may be added to the database to relate to the tattoo for subsequent matching. If a subsequent observer collects new images of the same tattoo, say 3 months later, these images will be compared to the original tattoo design and also to the images collected during prior successful identifications. Different weights may be used for each of the images collected in successful identification in order to avoid overfitting to irrelevant data such as by creating a composite image of the aging process. A pitfall of that method is that errors due to imaging quality may be recognized as tattoo aging and reduce the quality of the image identification by allowing false positives. This is partially mitigated by making image composites weighted based on image quality and by how recent the images are. Using this method in conjunction with the other methods cited in this document may enhance fit quality.

In some embodiments, tattoo aging may be simulated. The main degradation processes for tattoos are the diffusion of ink through chemical, physical and biological means and the change in optical properties of the skin. Over time, skin translucency and pigmentation may change and ink in the skin may diffuse. Some inks may also degrade and lose some vibrancy. As a result, a tattoo may appear diffusing and fading over time. A simulation of this process may be possible using diffusion equation and by modeling the optical properties of the skin and the ink. While the speed of the degradation depends upon tattoo age, environmental factors, life habits and varies from individual to individual, the model of degradation is fairly similar. It is therefore possible to extrapolate a set of possible degradation outcomes which would depend on tailorable variables associated with the unknown factors of aging speed, environment effects, lifestyle effects and individual phenotype effects. As a result, a match with a current tattoo image may be reached by estimating how an original tattoo would look like by searching that variable set and solving the inverse degradation problem designed to answer the following question: which set of degradation parameters would improve fit between the current image of the tattoo and the original design?

A simulation method can both benefit from the continuous data accretion process described above as well as improve its quality of image matching. Indeed, if current images fit with the original model without a simulation of degradation (i.e., the fit residual is smaller than the failure threshold), a first estimate of the degradation variable may be found which may help predict future degradation. Conversely, fit residuals may be mitigated by separating residuals that minimize the constitutive degradation model (i.e., residual compatible with the understanding of the tattoo degradation model) and orthogonal residuals (i.e., residuals that can't be explained by the degradation model, which may come from imaging errors), which may further improve fitness and avoid the pitfall of the continuous data accretion method of overfitting on orthogonal residuals.

Overall, a simulation model can improve the fit of images with the original design by providing an educated guess as to how a tattoo looks now based on the known degradation processes.

In some embodiment, a high-quality scan of the tattoo after aging is used to establish a new reference to compare identification images against. In some cases, the degradation of a tattoo is to the point that no match is possible. In these cases, the tattoo owner may need to get their tattoo scanned by the NFT minter or its operator to re-establish a reference image. For this process, the tattoo owner is first identified as the legitimate NFT holder by checking wallet ownership. It is also possible to use the high-quality imaging equipment to image the skin texture such as epidermal folds to ascertain authenticity, something currently out of reach of most personal imaging devices. Once identification is ascertained, the tattoo may be scanned with high-definition equipment such as a high-resolution camera under appropriate lighting. This high-resolution image is appended to the database used for image matching of FIGS. 6A and 6B and becomes a reference against which subsequent identification methods will rely for authentication.

In some embodiments, even with access to high quality scans, it may not be possible to establish the uniqueness of a tattoo. For example, a very popular tattoo may be difficult to distinguish from another copy of the same tattoo design after many years of aging. In these instances, it may be favorable to perform a touch-up for the purpose of adding uniquely identifiable features to an existing tattoo. These touch-ups may be constituted of several additional dots added to the design that can encode for a unique match. These dots may be blended in the existing design by approximating aging so as not to look out of place. These touchups may also be done through highlights of the existing design to improve the aesthetic quality of the tattoo. A high-definition image of the resulting tattoo may then be taken to become the new image reference, or a composite design may be digitally generated including the old tattoo design appended with the new punctures. This method adds new content to an existing tattoo for the purpose of making it easier to identify using an imaging-based authentication method.

The identification method presented in relation to FIGS. 6A and 6B allows to uniquely associate a picture of a tattoo with a database entry or NFT ID using image analysis and peer to peer identification and/or validation. Because of this unique association, it is possible to relate digital content with a tattoo on skin.

At the lowest level, this may consist of typical metadata associated with a specific NFT, such as an image of the tattoo design, the name of the design, it's artist, date of execution, price of NFT and so on. However, it is also possible to define additional metadata in the form of a hyperlink or remote content. This opens the opportunity to associate a physical tattoo on skin with digital content such as images, film, text or executable programs and applications. Further, modification of this content may be restricted to the NFT owner, the NFT minting party, the service provider or any other authorized party.

One embodiment of the invention is to use this uniquely associated digital content to a tattoo for multistep verification of authorization. The tattoo can indeed be used as a cryptographic key, together with wallet recognition to uniquely identify an authorized individual, for example to access a restricted area or to operate machinery, to review data or to access a program, server, online account and so on. This method of multistep authorization is similar to biometric identification together with wallet identification, especially if unique fine skin features are identified visually on the tattoo, with the difference that the identity of the tattoo owner (name, physical features other than the tattoo, like face and so on) may never be revealed or used during this process of authorizing access. Note that the same tattoo may be employed by various restricted access observers by embedding their own cryptographic method within the digital content stored through the NFT associated with the tattoo, for example the digital content associated with the tattoo could contain a 'keychain' of various credentials or passkeys.

An example of this embodiment is for the tattoo owner to log in their locked cell phone. Rather than using their face for unlocking their phone they may use their tattoo for unlocking their cellphone.

Another embodiment of the invention is to provide digital augmentation to a physical tattoo. Indeed, the additional data associated with the NFT may contain data such as text, images, 3D models or animations that could be overlaid over the physical tattoo using augmented reality displayed on an observer's personal computing and imaging device or VR set. This augmented reality rendering may be static (i.e., constructed over a picture of the tattoo) or dynamic (i.e., on real time video feed from the tattoo and the body of the tattoo owner). In this embodiment, the tattoo pattern is used as a fiducial marker for the identification of the body part position, distance, parallax and so on, such that the stitched augmented reality digital content can be appropriately displayed on a screen of a personal computing and imaging device. By this, we mean that the augmented reality display gives the illusion that the displayed digital content is part of the imaged scene.

For example, this can be used in the case of a tattooed 'mood ring'. Say that a tattoo owner has a tattooed 'mood ring' on their forearm. The tattoo owner may access applications on their personal computing device to associate digital content to the tattoo of the 'mood ring', for example an animation of smiling face. A third-party observer may use their imaging and computing device to image and identify the 'mood ring' tattoo using the tattoo identification and authentication method presented in this disclosure. If authorized by the tattoo owner, the observer may be able to access the associated digital content with the 'mood ring' tattoo. In this case this corresponds to an animation of a three-dimensional smiling face that is projected in augmented reality over the image of the 'mood ring'. What's more, the tattoo owner may update and modify the digital content in real-time. For this example, the tattoo owner may be notified that a third party is accessing the digital content and adds the text 'what's up?' to the digital content and changes the animation from a smiling face to a winking face animation. This content is immediately updated on the third-party imaging display. The text 'what's up' may be overlaid to the image or be displayed in an integrated messenger application executed from the metadata. The third party may also be able to modify or append the digital information of the same tattoo, but this may be with restricted access such as the possibility to comment about the content without changing the tattoo owner 'post'. For instance, the third party may answer 'I am gr8 ☺!'.

In some embodiment, access to specific metadata content may require authentication of the observer. For example, the access may be public or may conversely allow authorized observers. In some embodiment, the digital content may be produced by a third party and uploaded by the tattoo holder before it can be displayed and shared. Examples of third-party content may be custom art, videogames, videogame characters, executable applications, vouchers, event passes and so on. For example, two individuals with enabled tattoos may play with or against each other in a videogame and see their characters superimposed on their tattoo. For example, in a monster trainer battle.

Finally, in some embodiment, the various tattoos on a person's skin may be used as their social media wall, onto which each tattoo may behave as dynamically updatable posts, accessible if imaged by a third-party observer. In some embodiment, third party observers may be able to review previously imaged tattoos and their current posts. In another embodiment, users may share images of their tattoos to share the associated posts.

Note that many of the processes and methods presented in this disclosure refer to NFTs held in a cryptographic chain. The intent of a cryptographic chain is to ensure certification through consensus when trust between actors is not achievable. In some embodiments, it may be possible to centrally control all actions regarding the tokens. It is straight forward to apply all the methods cited herein within a centrally held database where a blockchain may not be used. As a result, all methods presented herein that apply to NFT may also apply to centrally held database entries and wallets and NFT owner, buyer and observer may equally be database profiles and clients.

In some embodiments, the automated tattoo machine interacts with the NFT smart contract to authenticate the owner and verify NFT consumability. Here, a method is presented to detail how a service execution machine can execute a service using smart contract function on the blockchain for authentication and execution file from a database. In some embodiments, the service is the application of a tattoo on skin and the service execution machine is an automated tattoo machine. The purpose of this method is to provide, for example, a trustless method that removes the possibility of replication of a service without authorization at the machine level.

This method relies on tamper resistant PUF electronics for the encryption of messages and the signing of message by a wallet ID embedded into the service execution machine (e.g., machine 470 in FIG. 4 or tattooing apparatus 52 in FIG. 1A). Both the machine and database are operators of the NFT smart contract associated with the service. The database may hold the public keys for encryptions to communicate with approved service execution machines.

First, the machine receives a signed message from the NFT owner for the execution of the service. The message may contain an in-person cryptographic signature to make sure that the NFT owner is interacting with the machine. For example, this message may be the signed in-person verification data discussed in step 331 of FIG. 3. The machine may then communicate with the database to request the files associated with the NFT ID for the execution of the service. This request may contain the machine ID, the NFT ID, the in-person verification data and the cryptographic signature from the NFT owner. The database verifies that the machine ID is an allowed operator of the NFT, that the owner's digital signature on the verification data is valid and that the wallet owner does own the NFT in question by querying functions in the smart contract. The database then transmits the execution files to the service execution machine in an encrypted manner using the public key of the machine and its own private key (e.g., the address "serviceProvider" discussed in step 323). In the context of automatic tattooing, the encrypted execution files may be an encrypted digital tattoo file, which contains the data to robotically create a high-fidelity tattoo of the artwork 102 on skin, while a lower-resolution rendering of the artwork 102 may be available for public access as a part of the NFT for previewing of the artwork. The database may then interact with the smart contract of the NFT to flag the transmission of the execution files. This may then require that the machine interact with the smart contract at posteriori to confirm the execution or the failure of execution of the service in question. Once the machine receives the encrypted file, the machine then decrypts the file and calculates the file's hash. The file's hash is then compared to the file's hash listed in the smart contract metadata to verify integrity. Failure in the integrity may lead to the end of the process or a new request for database transfer. The file may then be operated by the machine with confirmation of by both the service provider and the person receiving the service that this service corresponds to the wanted service. For example, and in the case of tattooing, the tattoo seeker may verify that the wanted tattoo is the one loaded in the automated tattoo machine by reviewing the tattoo rendering. At completion of the service, the machine may sign a proof of completion message delivered to the smart contract.

This method may be used across embodiments of the inventions that may use a service execution machine, such as the automated tattoo machine, to enhance uniqueness of the execution of tattoos at the machine level.

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A robotic tattooing apparatus comprising:
   a tattoo device having at least one needle;
   an actuator assembly configured to move the tattoo device along a subject; and
   an optical tattoo analyzer configured to capture one or more images of a tattoo applied to skin of the subject;
   a controller in communication with the actuator assembly and the optical tattoo analyzer, the controller is programmed to
      identify, via a cryptographic signature, the subject as an owner of artwork associated with a cryptographic token to be applied,
      in response to identifying the subject as the owner, control the robotic tattooing apparatus to apply the tattoo of the artwork using the tattoo device;
      capture one or more authentication images of the applied tattoo using the optical tattoo analyzer; and
      authenticate the applied tattoo based on the artwork and the captured one or more authentication images.

2. The robotic tattooing apparatus of example 1, further comprising applying the tattoo according to tattoo command instructions hashed or included in a NFT governed by a smart contract, linked to the artwork, wherein the tattoo command instructions are stored in a database.

3. The robotic tattooing apparatus of any of examples 1-2, further comprising rejecting the application of the tattoo on the skin according to a number of times the tattoo can be applied in instructions included in a NFT governed by a smart contract.

4. The robotic tattooing apparatus of any of examples 1-3, wherein the optical tattoo analyzer includes a machine vision device configured to capture color images of the tattoo after the tattoo has been applied.

5. The robotic tattooing apparatus of any of examples 1-4, wherein the controller is programmed to:
   analyze the captured one or more authentication images to identify one or more unique features described in tattoo information associated with an NFT governed by a smart contract;
   calculate a confidence index based on a number of unique features identified on the captured one or more authentication images;
   display, the confidence index; and
   establish, based on the confidence index, authenticity that the tattoo is related to the NFT governed by the smart contract.

6. The robotic tattooing apparatus of any of examples 1-5, further comprising:
   capturing one or more images of the tattoo based on imaging settings of an authentication protocol selected based on a predicted resolution of visible puncture parameters of the tattoo;
   determining one or more unique features of the tattoo based on the one or more images of the tattoo; and
   determining the authentication protocol based on one or more unique features of the tattoo.

7. The robotic tattooing apparatus of any of examples 1-6, wherein the authentication protocol includes one or more of a threshold number of pixels per area, color rendering, and/or signal to noise ratio.

8. The robotic tattooing apparatus of any of examples 1-7, wherein the applied tattoo includes one or more machine-readable identification features.

9. The robotic tattooing apparatus of any of examples 1-8, wherein the one or more authentication images include one or more unique machine-identifiable features incorporated into the tattoo not affecting a design aesthetic.

10. The robotic tattooing apparatus of any of examples 1-9, wherein the robotic tattooing apparatus comprises tamper hardened electronics for cryptographically verifying artwork ownership and right to consume.

11. A computer-implemented method comprising:
identifying, via a cryptographic signature, a subject as an owner of artwork associated with a cryptographic token to be applied;
in response to identifying the subject as the owner, controlling a robotic tattooing apparatus to apply the tattoo of the artwork using a tattoo device;
capturing one or more authentication images of the applied tattoo using an optical tattoo analyzer; and
authenticating the applied tattoo based on the artwork and the captured one or more authentication images.

12. The computer-implemented method of any of example 11, further comprising:
applying the tattoo according to tattoo command instructions hashed or included in an NFT governed by a smart contract, linked to the artwork, wherein the tattoo command instructions are stored in a database.

13. The computer-implemented method of any of examples 11-12, further comprising:
rejecting the application of the tattoo on skin according to a number of times the tattoo can be applied in instructions included in an NFT governed by a smart contract.

14. The computer-implemented method of any of examples 11-13, further comprising:
analyzing the captured one or more authentication images to identify one or more unique features described in tattoo information associated with an NFT governed by a smart contract;
calculating a confidence index based on a number of unique features identified on the captured one or more authentication images;
displaying, the confidence index; and
establishing, based on the confidence index, authenticity that the tattoo is related to the NFT governed by the smart contract.

15. The computer-implemented method of any of examples 11-14, wherein the optical tattoo analyzer includes a machine vision device configured to capture color images of the tattoo after the tattoo has been applied.

16. A system comprising:
one or more processors; and
one or more memories storing instructions that, when executed by the one or more processors, cause the system to perform a process comprising:
identifying, via a cryptographic signature, a subject as an owner of artwork associated with a cryptographic token to be applied;
in response to identifying the subject as the owner, controlling a robotic tattooing apparatus to apply the tattoo of the artwork using a tattoo device;
capturing one or more authentication images of the applied tattoo using an optical tattoo analyzer; and
authenticating the applied tattoo based on the artwork and the captured one or more authentication images.

17. The system according to example 16, wherein the process further comprises:
applying the tattoo according to tattoo command instructions hashed or included in a NFT governed by a smart contract, linked to the artwork, wherein the tattoo command instructions are stored in a database.

18. The system according to any of examples 16-17, wherein the process further comprises:
rejecting the application of the tattoo on skin according to a number of times the tattoo can be applied in instructions included in a NFT governed by a smart contract.

19. The system according to any of examples 16-18, wherein the process further comprises:
analyzing the captured one or more authentication images to identify one or more unique features described in tattoo information associated with an NFT governed by a smart contract;
calculating a confidence index based on a number of unique features identified on the captured one or more authentication images;
displaying, the confidence index; and
establishing, based on the confidence index, authenticity that the tattoo is related to the NFT governed by the smart contract.

20. The system according to any of examples 16-19, wherein the optical tattoo analyzer includes a machine vision device configured to capture color images of the tattoo after the tattoo has been applied.

21. A computer-implemented method for managing ownership of a digital image of a tattoo associated with a Non-Fungible Token (NFT), the computer-implemented method comprising:
creating, via a digital market interface on a user device, the NFT governed by a smart contract on a blockchain, wherein the NFT includes hash of the tattoo information and tattoo command instructions, stored in a database, operational by a robotic tattoo machine;
in response to a transaction on the blockchain, transferring the NFT to a first digital wallet of a current NFT owner;
determining the current NFT owner has an appointment or booking to have the tattoo applied on the skin of the current NFT owner by a robotic tattoo machine;
authenticating a user as the current owner of the NFT based on a cryptographic signature on a message, wherein the user signs the message with a private key of the wallet of the current NFT owner; and
in response to authenticating the user, applying by the robotic tattoo machine the tattoo on the skin of the user according to the tattoo information and tattoo command instructions hashed in the NFT and stored in the database.

22. The computer-implemented method of example 21, further comprising:
the current NFT owner realizing a secondary transaction with a second user by transferring the NFT from the first digital wallet to a second wallet of a second user, hereby making the second user the current NFT owner; and
where subsequent transfers remain possible between the current NFT owner and a series of subsequent wallet owners as long as the transfer is not locked.

23. The computer-implemented method of example 21, further comprising:
capturing an image of the tattoo on the skin of the user;
analyzing the captured image of the tattoo to identify one or more unique features described in data associated with the NFT governed by the smart contract;
calculating a confidence index based on a number of unique features identified on the captured image; and establishing, based on the confidence index, authenticity that the tattoo is associated with the NFT.

24. The computer-implemented method of example 21, further comprising:
   authenticating the NFT and tattoo ownership by:
      receiving a wallet identification from the owner of the NFT; and
      verifying that the tattoo design associated with the NFT has been tattooed on the skin of the user that provided the wallet identification.

25. The computer-implemented method of example 21, further comprising:
   in response to booking the tattoo, locking the NFT on the blockchain to restrict transfer of the NFT.

26. The computer-implemented method of example 21, further comprising:
   in response to applying a tattoo, modifying the NFT on the blockchain to consume rights to tattooing services associated with the NFT 27. The computer-implemented method of example 21, further comprising:
   prior to application of the tattoo by the machine, checking whether the rights to tattooing services are consumed by reading data from the NFT; and
   blocking the application of the tattoo by the machine if the rights to tattooing services are consumed.

28. The computer-implemented method of example 21, further comprising:
   validating the ownership of the NFT by:
      sending the message to the digital market interface on the user device;
      receiving the cryptographic signature on the message by the user with the private key of the wallet of the current NFT owner; and
      verifying the cryptographic signature with the public key of the wallet of the current NFT owner.

29. The computer-implemented method of example 21, further comprising:
   locking the NFT transfer by the current NFT owner on the blockchain; and
   transferring, by an NFT administrator, the locked NFT from the first wallet to a second wallet on the blockchain without a payable transaction by:
      approving the transfer by the NFT administrator based on receiving a cryptographically signed message as authorization from the NFT owner; and
      determining the NFT transfer is within an expected use specified in the smart contract.

30. The computer-implemented method of example 21, wherein the tattoo command instructions include one or more of puncture locations, needle height, volume of ink applied, needle speed, ink dot position and depth, ink type, number of punctures, or fiducial stenciling associated with applying the tattoo by the robotic tattoo machine.

31. A system comprising:
   one or more processors; and
   one or more memories storing instructions that, when executed by the one or more processors, cause the system to perform a process for managing ownership of a digital tattoo design associated with a Non-Fungible Token (NFT), the process comprising:
      creating, via a digital market interface on a user device, the NFT governed by a smart contract on a blockchain, wherein the smart contract includes hash of the tattoo information and tattoo command instructions, stored in a database, operational by a robotic tattoo machine;
      in response to a transaction on the blockchain, transferring the NFT to a first digital wallet of a current NFT owner;
      determining the current NFT owner has an appointment or booking to have the robotic tattoo machine apply on a skin of the current NFT owner the tattoo;
      authenticating a user as the current owner of the NFT based on a cryptographic signature on a message, wherein the user signs the message with a private key of the wallet of the current NFT owner; and
      in response to authenticating the user, applying by the robotic tattoo machine the tattoo on the skin of the user according to the tattoo information and tattoo command instructions hashed in the NFT and stored in the database.

32. The system according to example 31, wherein the process further comprises:
   the current NFT owner realizing a secondary transaction with a second user by transferring the NFT from the first digital wallet to a second wallet of a second user, hereby making the second user the current NFT owner and;
   where subsequent transfers remain possible between the current NFT owner and a series of subsequent wallet owners as long as the transfer is not locked.

33. The system of example 31, wherein
   Tamper resistant electronics is used for cryptographically signing operations of the smart contract governing the NFT.

34. The system of example 33, further comprising,
   the operations of the smart contract governing the NFT resulting in;
   accessing the tattoo information and instructions from the database;
   the locking of the NFT;
   the modifying of the NFT; and/or
   the burning of the NFT 35. The system according to example 31, wherein the process further comprises:
   capturing an image of the tattoo on the skin of the user;
   analyzing the captured image of the tattoo to identify one or more unique features described in data associated with the NFT governed by the smart contract;
   calculating a confidence index based on a number of unique features identified on the captured image; and
   establishing, based on the confidence index, authenticity that the tattoo is associated with the NFT.

36. The system according to example 31, wherein the process further comprises:
   authenticating the NFT and tattoo ownership by:
      receiving a wallet identification from the owner of the NFT; and
      verifying that the tattoo design associated with the NFT has been tattooed on the skin of the user that provided the wallet identification.

37. The system according to example 31, wherein the process further comprises:
   in response to booking the tattoo, locking the NFT on the blockchain to restrict transfer of the NFT.

38. The system according to example 31, wherein the process further comprises:
   in response to applying a tattoo, modifying the NFT on the blockchain to consume rights to tattooing services associated with the NFT.

39: The system according to example 31, wherein the process further comprises:

prior to application of the tattoo by the machine, checking whether the rights to tattooing services are consumed by reading data from the NFT; and blocking the application of the tattoo by the machine if the rights to tattooing services are consumed.

40. The system according to example 31, wherein the process further comprises:

validating the ownership of the NFT by:
sending the message to the digital market interface on the user device;
receiving the cryptographic signature on the message by the user with the private key of the wallet of the current NFT owner; and
verifying the cryptographic signature with the public key of the wallet of the current NFT owner.

41. The system according to example 31, wherein the process further comprises:

locking the NFT transfer by the NFT owner on the blockchain; and
transferring, by an NFT administrator, the locked NFT from the first wallet to a second wallet on the blockchain without a payable transaction by:
approving the transfer by the NFT administrator based on receiving a cryptographically signed message as authorization from the NFT owner; and
determining the NFT transfer is within an expected use specified in the smart contract.

42. The system according to example 31, wherein the tattoo command instructions include one or more of puncture locations, needle height, volume of ink applied, needle speed, ink dot position and depth, ink type, number of punctures, or fiducial stenciling associated with applying the tattoo by the robotic tattoo machine.

43. A non-transitory computer-readable medium storing instructions that, when executed by a computing system, cause the computing system to perform operations for managing ownership of a digital tattoo design associated with a Non-Fungible Token (NFT), the operations comprising:

creating, via a digital market interface on a user device, the NFT governed by a smart contract on a blockchain, wherein the smart contract includes hash of the tattoo information and tattoo command instructions, stored in a database, operational by a robotic tattoo machine;
in response to a transaction on the blockchain, transferring the NFT to a first digital wallet of a current NFT owner;
determining the current NFT owner has an appointment or booking to have the robotic tattoo machine apply on a skin of the current NFT owner the tattoo;
authenticating a user as the current owner of the NFT based on a cryptographic signature on a message, wherein the user signs the message with a private key of wallet of the current NFT owner; and
in response to authenticating the user, applying by the robotic tattoo machine the tattoo on the skin of the user according to tattoo information and tattoo command instructions hashed in the NFT and stored in the database.

44. The non-transitory computer-readable medium of example 43, wherein the operations further comprise:

the current NFT owner realizing a secondary transaction with a second user by transferring the NFT from the first digital wallet to a second wallet of a second user, hereby making the second user the current NFT owner; and wherein subsequent transfers remain possible between the current NFT owner and a series of subsequent wallet owners as long as the transfer is not locked.

45. The non-transitory computer-readable medium of example 43, wherein the operations further comprise:

capturing an image of the tattoo on the skin of the user;
analyzing the captured image of the tattoo to identify one or more unique features described in data associated with the NFT governed by the smart contract;
calculating a confidence index based on a number of unique features identified on the captured image; and
establishing, based on the confidence index, authenticity that the tattoo is associated with the NFT.

46. The non-transitory computer-readable medium of example 43, wherein the operations further comprise:

authenticating the NFT and tattoo ownership by:
receiving a wallet identification from the owner of the NFT; and
verifying that the tattoo design associated with the NFT has been tattooed on the skin of the user that provided the wallet identification.

47. The non-transitory computer-readable medium of example 43, wherein the operations further comprise:

in response to booking the tattoo, locking the NFT on the blockchain to restrict transfer of the NFT.

48. The non-transitory computer-readable medium of example 43, wherein the operations further comprise:

in response to applying a tattoo, modifying the NFT on the blockchain to consume rights to tattooing services associated with the NFT.

49. The non-transitory computer-readable medium of example 43, wherein the operations further comprise:

prior to application of the tattoo by the machine, checking whether the rights to tattooing services are consumed by reading data from the NFT; and
blocking the application of the tattoo by the machine if the rights to tattooing services are consumed.

50. The non-transitory computer-readable medium of example 43, wherein the operations further comprise:

validating the ownership of the NFT by:
sending the message to the digital market interface on the user device;
receiving the cryptographic signature on the message by the user with the private key of the wallet of the current NFT owner; and
verifying the cryptographic signature with the public key of the wallet of the current NFT owner.

51. The non-transitory computer-readable medium of example 43, wherein the operations further comprise:

locking the NFT transfer by the NFT owner on the blockchain; and
transferring, by an NFT administrator, the locked NFT from the first wallet to a second wallet on the blockchain without a payable transaction by:
approving the transfer by the NFT administrator based on receiving a cryptographically signed message as authorization from the NFT owner; and
determining the NFT transfer is within an expected use specified in the smart contract.

52. A computer-implemented method for managing ownership of a digital tattoo design associated with a Non-Fungible Token (NFT), the computer-implemented method comprising:

authorizing tattooing of the digital tattoo design onto a user based on the user establishing ownership of the NFT;

obtaining tattoo instructions hashed in an NFT governed by a smart contract and stored in a database; and
tattooing the digital tattoo design onto the user using the obtained tattoo instructions.

53. The computer-implemented method of example 52, further comprising manually applying the tattoo using ink color information from the tattoo instructions.

54. The computer-implemented method of example 52, further comprising robotically applying the tattoo by executing the tattoo instructions using one or more processors.

55. The computer-implemented method of example 52, further comprising:
in response to completing the tattooing the digital tattoo design onto the user, burning the NFT.

56. The computer-implemented method of example 52, further comprising:
in response to completing the tattooing the digital tattoo design onto the user, consuming the tattooing service.

57. The computer-implemented method of example 52, further comprising:
imaging the applied tattoo on the user;
using at least one machine vision model trained using sets of tattoo images to authenticate the tattoo; and
in response to authenticating of the applied tattoo on the user, uniquely linking the tattoo to the user in a database.

58. The computer-implemented method of example 52, wherein the smart contract includes one or more tattoo-application criteria for burning the NFT or consuming the tattooing service.

59. The computer-implemented method of example 52, further comprising creating the NFT by
transmitting one or more tattoo instructions;
receiving a selection of the one or more tattoo instructions and artwork; and
minting the NFT, which includes the hashed tattoo instructions and artwork, and hyperlinks to the tattoo instruction and artwork stored in a database.

60. The computer-implemented method of example 52, further comprising:
sending a notification to a user for authenticating the tattooed digital artwork on the user;
receiving authentication data of the tattooed digital artwork; and
comparing the received authentication data to reference data to determine whether the tattooed digital artwork is authentic.

61. The computer-implemented method of example 52, wherein the authentication data includes one or more digital images of the tattooed digital artwork and the reference data is an image of the artwork.

62. A computer-implemented method for managing a digital tattoo design associated with a Non-Fungible Token (NFT), the computer-implemented method comprising:
applying by a robotic tattoo machine the tattoo on a user according to instructions hashed in the NFT governed by a smart contract and stored in a database;
updating a ledger on a blockchain to indicate the tattoo from the NFT was applied;
identifying, in the NFT, a number of times the digital tattoo design is permitted to be applied; and
burning the NFT after the digital tattoo design is applied the number of times.

63. A computer-implemented method for managing a digital tattoo design associated with a Non-Fungible Token (NFT), the computer-implemented method comprising:
applying by a robotic tattoo machine the tattoo on a user according to instructions hashed in the NFT governed by a smart contract and stored in a database;
updating a ledger on a blockchain to indicate the tattoo from the NFT was applied;
identifying, in the NFT, a number of times the digital tattoo design is permitted to be applied; and
Consuming the service of the NFT after the digital tattoo design is applied the number of times.

64. A computer-implemented method for managing tattooing via a Non-Fungible Token (NFT), the computer-implemented method comprising:
determining a user has an appointment or booking to have a robotic tattoo machine apply the tattoo on the user;
locking the NFT on a blockchain to prevent a transaction of the NFT;
determining the appointment or booking has been cancelled; and unlocking the NFT on the blockchain.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

The embodiments, features, systems, devices, materials, methods, machine-learning modules, and techniques described herein may, in some embodiments, be similar to any one or more of the embodiments, features, systems, devices, marketplaces, methods, technologies, and techniques described in the following: International Patent Application No. PCT/US2020/043588, International Patent Application No. PCT/US22/13691; U.S. application Ser. No. 17/584,011; and U.S. application Ser. No. 17/157,935, as well as other patents, publications, and applications referenced herein. All of the patents, publications, and applications referenced herein are incorporated by reference in their entireties. The systems and technologies disclosed herein can include the technologies in the incorporated by reference patents, publications, and applications. For example, the online tattoo marketplaces disclosed in International Patent Application No. PCT/US2020/043588, International Patent Application No. PCT/US22/13691; U.S. application Ser. No. 17/584,011; U.S. application Ser. No. 17/157,935 can be used to create, manage, book tattoo session, or otherwise manage NFTs, ledgers, payments, etc. The robotic systems of U.S. application Ser. No. 17/157,935 can apply tattoos associated with NFTs.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

It should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim in this or any application claiming priority to this application requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment.

While specific embodiments and applications of the present invention have been illustrated and described, it is to be understood that the invention is not limited to the precise configuration and components disclosed herein. Various modifications, changes, and variations, which will be apparent to those skilled in the art, may be made in the arrangement, operation, and details of the methods and systems of the present invention disclosed herein without departing from the spirit and scope of the invention.

We claim:

1. A robotic tattooing apparatus comprising:
    a tattoo device having at least one needle;
    an actuator assembly configured to move the tattoo device along a subject;
    an optical tattoo analyzer configured to capture one or more images of a tattoo applied to skin of the subject; and
    a controller in communication with the actuator assembly and the optical tattoo analyzer, the controller is programmed to
        identify, via a cryptographic signature, the subject as an owner of artwork associated with a cryptographic token to be applied;
        in response to identifying the subject as the owner, control the robotic tattooing apparatus to apply the tattoo of the artwork using the tattoo device;
        capture one or more authentication images of the applied tattoo using the optical tattoo analyzer;
        determine one or more unique features of the tattoo in the one or more authentication images of the applied tattoo; and
        authenticate the applied tattoo based on the artwork and the one or more unique features.

2. The robotic tattooing apparatus of claim 1, further comprising applying the tattoo according to tattoo command instructions hashed or included in a NFT governed by a smart contract, linked to the artwork, wherein the tattoo command instructions are stored in a database.

3. The robotic tattooing apparatus of claim 1, further comprising rejecting an application of the tattoo on skin according to a number of times the tattoo can be applied in instructions included in a NFT governed by a smart contract.

4. The robotic tattooing apparatus of claim 1, wherein the optical tattoo analyzer includes a machine vision device configured to capture color images of the tattoo after the tattoo has been applied.

5. The robotic tattooing apparatus of claim 1, wherein the controller is programmed to:
    analyze the captured one or more authentication images to identify the one or more unique features described in tattoo information associated with an NFT governed by a smart contract;
    calculate a confidence index based on a number of unique features identified on the captured one or more authentication images;
    display, the confidence index; and
    establish, based on the confidence index, authenticity that the tattoo is related to the NFT governed by the smart contract.

6. The robotic tattooing apparatus of claim 1, further comprising:
    capturing one or more images of the tattoo based on imaging settings of an authentication protocol selected based on a predicted resolution of visible puncture parameters of the tattoo; and
    determining the authentication protocol based on the one or more unique features of the tattoo.

7. The robotic tattooing apparatus of claim 6, wherein the authentication protocol includes one or more of a threshold number of pixels per area, color rendering, and/or signal to noise ratio.

8. The robotic tattooing apparatus of claim 1, wherein the applied tattoo includes one or more machine-readable identification features.

9. The robotic tattooing apparatus of claim 1, wherein the one or more authentication images include one or more unique machine-identifiable features incorporated into the tattoo not affecting a design aesthetic of the tattoo.

10. The robotic tattooing apparatus of claim 1, wherein the robotic tattooing apparatus comprises tamper hardened electronics for cryptographically verifying artwork ownership and right to consume.

11. A computer-implemented method comprising:
    identifying, via a cryptographic signature, a subject as an owner of artwork associated with a cryptographic token to be applied;
    in response to identifying the subject as the owner, controlling a robotic tattooing apparatus to apply the tattoo of the artwork using a tattoo device;
    capturing one or more authentication images of the applied tattoo using an optical tattoo analyzer;
    determining one or more unique features of the tattoo in the one or more authentication images of the applied tattoo; and
    authenticating the applied tattoo based on the artwork and the one or more unique features.

12. The computer-implemented method of claim 11, further comprising:
    applying the tattoo according to tattoo command instructions hashed or included in a NFT governed by a smart contract, linked to the artwork, wherein the tattoo command instructions are stored in a database.

13. The computer-implemented method of claim 11, further comprising:

rejecting the application of the tattoo on skin according to a number of times the tattoo can be applied in instructions included in a NFT governed by a smart contract.

14. The computer-implemented method of claim 11, further comprising:
analyzing the captured one or more authentication images to identify the one or more unique features described in tattoo information associated with an NFT governed by a smart contract;
calculating a confidence index based on a number of unique features identified on the captured one or more authentication images;
displaying, the confidence index; and
establishing, based on the confidence index, authenticity that the tattoo is related to the NFT governed by the smart contract.

15. The computer-implemented method of claim 11, wherein the optical tattoo analyzer includes a machine vision device configured to capture color images of the tattoo after the tattoo has been applied.

16. A system comprising:
one or more processors; and
one or more memories storing instructions that, when executed by the one or more processors, cause the system to perform a process comprising:
identifying, via a cryptographic signature, a subject as an owner of artwork associated with a cryptographic token to be applied;
in response to identifying the subject as the owner, controlling a robotic tattooing apparatus to apply the tattoo of the artwork using a tattoo device;
capturing one or more authentication images of the applied tattoo using an optical tattoo analyzer;
determining one or more unique features of the tattoo in the one or more authentication images of the applied tattoo; and
authenticating the applied tattoo based on the artwork and the one or more unique features.

17. The system according to claim 16, wherein the process further comprises:
applying the tattoo according to tattoo command instructions hashed or included in a NFT governed by a smart contract, linked to the artwork, wherein the hashed tattoo command instructions are stored in a database.

18. The system according to claim 16, wherein the process further comprises:
rejecting the application of the tattoo on skin according to a number of times the tattoo can be applied in instructions included in a NFT governed by a smart contract.

19. The system according to claim 16, wherein the process further comprises:
analyzing the captured one or more authentication images to identify the one or more unique features described in tattoo information associated with an NFT governed by a smart contract;
calculating a confidence index based on a number of unique features identified on the captured one or more authentication images;
displaying, the confidence index; and
establishing, based on the confidence index, authenticity that the tattoo is related to the NFT governed by the smart contract.

20. The system according to claim 16, wherein the optical tattoo analyzer includes a machine vision device configured to capture color images of the tattoo after the tattoo has been applied.

* * * * *